United States Patent
Zoll et al.

(10) Patent No.: US 11,058,416 B2
(45) Date of Patent: Jul. 13, 2021

(54) DEVICES AND METHODS FOR SECURING AN IMPLANT

(71) Applicant: Boston Scientific Scimed, Inc., Maple Grove, MN (US)

(72) Inventors: Jonathan Zoll, Providence, RI (US); Peter J. Pereira, Mendon, MA (US); Timothy P. Harrah, Cambrige, MA (US); Michael S. H. Chu, Brookline, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 521 days.

(21) Appl. No.: 14/704,611

(22) Filed: May 5, 2015

(65) Prior Publication Data
US 2015/0320537 A1    Nov. 12, 2015

Related U.S. Application Data

(60) Provisional application No. 61/989,842, filed on May 7, 2014.

(51) Int. Cl.
| | | |
|---|---|---|
| A61B 17/04 | (2006.01) | |
| A61F 2/00 | (2006.01) | |
| A61B 17/06 | (2006.01) | |
| A61B 17/00 | (2006.01) | |
| A61B 17/062 | (2006.01) | |
| A61B 17/064 | (2006.01) | |

(52) U.S. Cl.
CPC ...... *A61B 17/0487* (2013.01); *A61B 17/0401* (2013.01); *A61B 17/0469* (2013.01); *A61B 17/06004* (2013.01); *A61B 17/06066* (2013.01); *A61F 2/0063* (2013.01); *A61B 17/0625* (2013.01); *A61B 17/0643* (2013.01); *A61B 2017/00805* (2013.01); *A61B 2017/0409* (2013.01); *A61B 2017/0417* (2013.01); *A61B 2017/0472* (2013.01); *A61B 2017/0488* (2013.01); *A61B 2017/06009* (2013.01); *A61F 2/0045* (2013.01); *A61F 2002/0072* (2013.01)

(58) Field of Classification Search
CPC ............ A61B 17/0487; A61B 17/0401; A61B 17/06066; A61B 17/06004; A61B 17/0625; A61B 17/0643; A61B 2017/0488; A61B 2017/0472; A61B 2017/0417; A61B 2017/0409; A61B 2017/00805; A61B 2017/06009; A61F 2/0045; A61F 2002/0072
See application file for complete search history.

(56) References Cited

U.S. PATENT DOCUMENTS 3,600,027 A * 8/1971 Noland ............. B65D 63/1027
                                                       24/16 PB
3,881,759 A * 5/1975 Fuehrer ................. F16B 21/071
                                                       292/321
(Continued)

*Primary Examiner* — Kaylee R Wilson
(74) *Attorney, Agent, or Firm* — Brake Hughes Bellermann LLP

(57) ABSTRACT

In one embodiment, a medical device includes a needle and a catch. The catch has a body portion. The body portion of the catch defines a cavity. The catch is configured to be coupled to the needle such that at least a portion of the needle is disposed within the cavity.

18 Claims, 25 Drawing Sheets

(56) References Cited

U.S. PATENT DOCUMENTS

| | | | | |
|---|---|---|---|---|
| 6,015,428 | A * | 1/2000 | Pagedas | A61B 17/0483 606/232 |
| 8,709,021 | B2 | 4/2014 | Chu et al. | |
| 2004/0138682 | A1* | 7/2004 | Onuki | A61B 17/0401 606/144 |
| 2004/0186515 | A1* | 9/2004 | Rosenblatt | A61B 17/0487 606/228 |
| 2007/0162052 | A1* | 7/2007 | Hashimoto | A61B 17/06114 606/139 |
| 2007/0173864 | A1 | 7/2007 | Chu | |
| 2009/0005793 | A1* | 1/2009 | Pantages | A61B 17/06004 606/144 |
| 2009/0259251 | A1* | 10/2009 | Cohen | A61B 17/06166 606/228 |
| 2011/0071548 | A1* | 3/2011 | Yeh | A61B 17/0057 606/144 |
| 2012/0330356 | A1* | 12/2012 | Rosenberg | A61B 17/0401 606/232 |

\* cited by examiner

DEVICES AND METHODS FOR SECURING AN IMPLANT

CROSS-REFERENCE TO RELATED APPLICATION

This application is a Nonprovisional of, and claims priority to, U.S. Patent Application No. 61/989,842, filed on May 7, 2014, entitled "DEVICES AND METHODS FOR SECURING AN IMPLANT", which is incorporated by reference herein in its entirety.

TECHNICAL FIELD

This disclosure relates generally to medical devices and more particularly to devices that are configured to help secure an implant within a body of a patient and methods for placing such devices within the body of the patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension of a portion of a body of a patient. For example, a hysterocele is often treated with a hysterectomy followed by a vaginal vault suspension. In some cases a sacrocolpopexy may be performed. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the implant used, pelvic floor repair can require various fixation locations within a pelvic region. For example, an implant can be secured using a number of anchors disposed at various fixation points.

It may be difficult to secure the implants within body of the patient at the various attachment locations. For example, in some cases the depth of penetration of the attachment tissue may be critical.

SUMMARY

In one embodiment, a medical device includes a needle and a catch. The catch has a body portion. The body portion of the catch defines a cavity. The catch is configured to be coupled to the needle such that at least a portion of the needle is disposed within the cavity.

In another embodiment, a medical device includes a delivery tool, a needle, and a catch. The delivery tool has a receiving portion and a carrier portion. The needle is configured to be removably coupled to the carrier portion of the delivery tool. The catch has a body portion. The body portion of the catch defines a cavity. The catch is configured to be coupled to the needle such that at least a portion of the needle is disposed within the cavity. The catch is configured to be removably coupled to the receiving portion of the delivery tool.

In another embodiment, a method of coupling an implant to bodily tissue of a patient includes inserting a device into a body of the patient, the device having a delivery tool, a catch removably coupled to a first portion of the delivery tool, and a needle removably coupled to a second portion of the delivery tool; passing the needle through the implant and bodily tissue; coupling the needle to the catch; removing the needle from the second portion of the delivery tool; and removing the catch from the first portion of the delivery tool.

DETAILED DESCRIPTION

Figure 1:
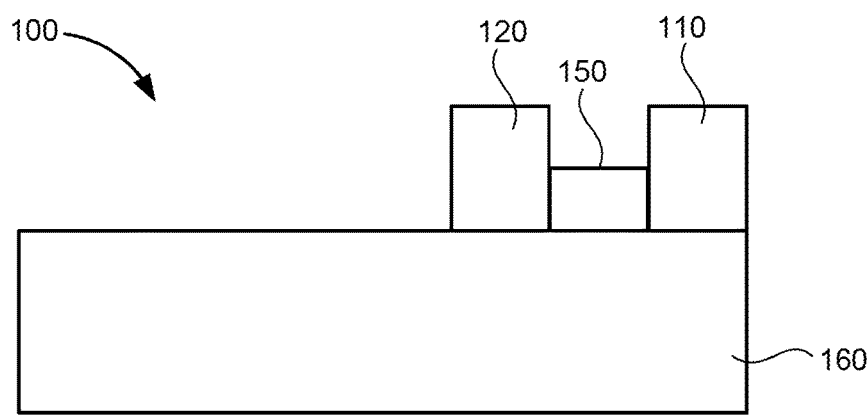
FIG. 1 is a schematic illustration of a device according to an embodiment of the invention.

The devices and methods described herein are generally directed to implants configured to be disposed within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a vaginal wall or vaginal tissue proximate a vaginal wall, a sacrospinous ligament, or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient. The implants and procedures described herein may be used in a female patient or a male patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

The implants described herein can be delivered to various parts of the body of the patient using a variety of different method and delivery devices. The implants and methods disclosed herein include pelvic floor implants, but the implants may be configured to be placed and methods may be used to place such implants in any portion of the body of the patient.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

An implant can be delivered to a pelvic region of a patient using a variety of different delivery devices, only some examples of which are described herein.

FIG. 1 is a schematic illustration of a medical device 100 according to an embodiment of the invention. The medical device 100 includes a needle or needle member 110 and a catch or catch member 120. The medical device 100 also includes a coupling member 150 extending from the needle 110 to the catch 120. In the illustrated embodiment, the medical device also includes a delivery tool or delivery device 160.

The needle or needle member 110 is configured to be passed through bodily tissue. In some embodiments, the needle 110 is configured to be removably coupled to a portion of the delivery tool 160. For example, in some embodiments, the needle 110 is configured to be removably coupled to a distal portion or distal end portion of the delivery tool 160. In some embodiments, distal portion (or the portion of the delivery tool that the needle 110 is coupled to) is configured to advance the needle 110 through the bodily tissue.

In some embodiments, the needle 110 is configured to be removably coupled to a carrier portion of the delivery tool 160. In some embodiments, the carrier portion of the delivery tool 160 is configured to move with respect to an elongate portion of the delivery tool 160 to advance the needle 110 through bodily tissue. Specifically, the delivery tool 160 may be inserted into the body of the patient such that the needle 110 is disposed adjacent bodily tissue. The carrier may then be moved (such as via an actuator) to move or advance the needle 110 through the bodily tissue.

The catch or catch member 120 is configured to receive a portion of the needle 110 and capture or couple to a portion of the needle 110. In some embodiments, the catch or catch member 120 is configured to be fixedly or permanently coupled to the needle 110. In other embodiments, the catch or catch member 120 is configured to be removably coupled to the needle 110.

In some embodiments, the catch or catch member 120 is removably coupled to the delivery tool 160. For example, in some embodiments, the catch or catch member 120 is removably coupled to a portion of the delivery device or tool 160 at a location proximal of the portion to which the needle 110 is coupled. In other embodiments, the catch or catch member 120 is removably coupled to a portion of the delivery device or tool 160 that is at a location distal of the portion to which the needle 110 is coupled. Any type of removable connection may be used to removably couple the catch or catch member 120 to a portion of the delivery device or tool 160. For example, the catch 120 may be frictionally coupled to the delivery device 160 or may be slidably coupled to the delivery device 160. Other types of connections or couplings will be described in detail below.

In some embodiments, the catch or catch member 120 is configured to receive the needle 110 after the needle has passed though bodily tissue. Accordingly, in some embodiments, the medical device 100 may be inserted into the body of the patient such that the needle 110 and the catch 120 are disposed on opposite sides of bodily tissue (or such that some bodily tissue is disposed between the needle 110 and the catch 120). In some embodiments, the device 100 may be used to secure or help secure an implant within a body of the patient. In some such embodiments, the medical device 100 may be inserted into a body of a patient such that bodily tissue and a portion of the implant are disposed between the needle 110 and the catch 120.

The needle 110 may then be advanced through the bodily tissue (and the implant) and into a receiving portion of the catch 120. In some embodiments, such insertion of the needle 110 into a portion of the catch 120 causes the needle 110 to be coupled or attached to the catch 120. The carrier or portion of the delivery device 160 that is removably coupled to the needle may then release the needle. The catch or catch member 120 may also be released from the delivery device 160. The delivery device 160 may then be removed from the body thereby leaving the needle 110 and the catch 120 disposed within the body of the patient.

In the illustrated embodiment, a coupling member 150 extends from the catch 120 to the needle 110. The coupling member 150 may be any type of elongate member such as a filament, a suture, an elastic, a line, or a string. In other embodiments, the coupling member 150 is another type of device that extends from the needle 110 to the catch 120.

In the illustrated embodiment, the coupling member 150 has a first end portion that is coupled to the needle 110 and a second end portion that is couple to the catch 120. Thus, when the needle 110 is passed through bodily tissue (and an implant) and is coupled to the catch 120 (as described above), the catch 120, needle 110, and coupling member 150 will collectively form a loop or circle about the tissue and implant to couple or help couple the implant to the bodily tissue. In some embodiments, a portion of member 150 protrudes from catch 120. A physician may pull on the portion of the member 150 that is protruding from the catch 120 to cause the length of the member 150 between the needle 110 and catch 120 to shorten. Accordingly, the member 150 is synched down on the tissue or tissue and implant. In some embodiments, a tissue piercing portion of the needle 110 is disposed within or surrounded by the catch 120 when the needle 110 is coupled to the catch 120.

Figure 2A:
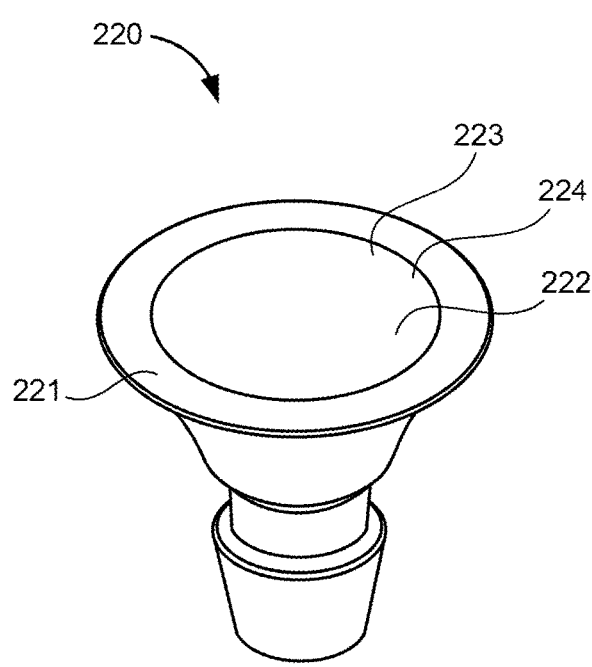
FIG. 2A is a perspective view of a catch according to an embodiment of the invention.
Figure 2B:
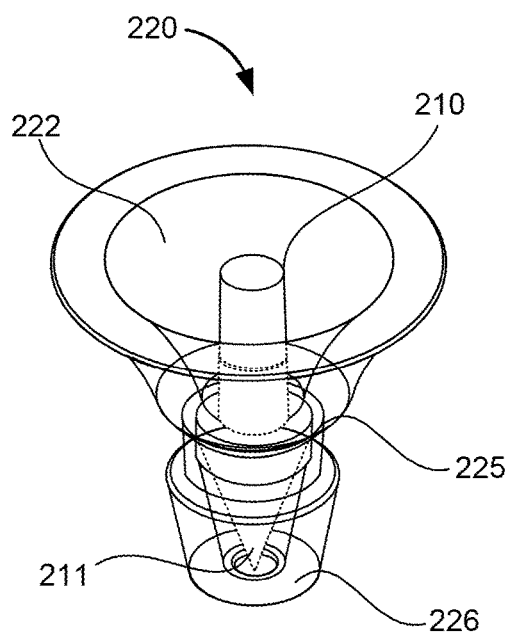
FIG. 2B is a see-though view of the catch of FIG. 2A.

FIG. 2A is a perspective view of a catch 220 according to an embodiment of the invention. FIG. 2B is a see-though view of the catch 220 coupled to a needle 210. The catch 220 includes a receiving portion 221. Specifically, the catch 220 defines a cavity 222 and an opening 223 in communication with the cavity 222. As best illustrated in FIG. 2B, the receiving portion 221 is configured to receive the needle 210 such that the needle 210 is received into the cavity 222 through the opening 223.

In the illustrated embodiment, the catch 220 includes a sidewall 224 that defines the cavity 222. The sidewall 224 defines a conical or funnel type or shaped cavity. In the some embodiments, the sidewall 224 is configured to contact the needle 210 to frictionally couple the needle 210 to the catch 220. Accordingly, the needle 210 is configured to be moved into the catch in one direction, but is retained within the cavity 222 and prevented from moving in an opposite direction. In the illustrated embodiment, the sidewall 224 includes a projection or a rib 225 that is configured engage the needle 210 to help couple the needle 210 to the catch 220. In some embodiments, the sidewall includes a plurality of projections or ribs.

In the illustrated embodiment, the needle 210 includes a tissue piercing portion 211. As best illustrated in FIG. 2B, the catch 220 is configured to couple to the needle 210 such that the tissue piercing portion 211 of the needle 210 is disposed within the cavity 222 defined by the catch 220. In other words, the distal end portion or the tissue piercing portion 211 of the needle does not extend from the catch 220.

In the illustrated embodiment, the catch 220 includes a base portion 226. The base portion 226 of the catch 220 provides a surface to contact or otherwise prevent the tissue piercing portion 211 of the needle 210 from extending from the catch 220.

In the illustrated embodiment, the funnel shape or the funnel like shape of the catch 220 (or the sidewall 224 of the catch) help facilitate the guiding of the needle 210 into the cavity 222 of the catch 220. Specifically, as the needle 220 enters the cavity 222, if the needle 210 happens to contact the sidewall 224, the needle 210 will be guided or forced towards the center of the cavity 222.

Figure 3A:
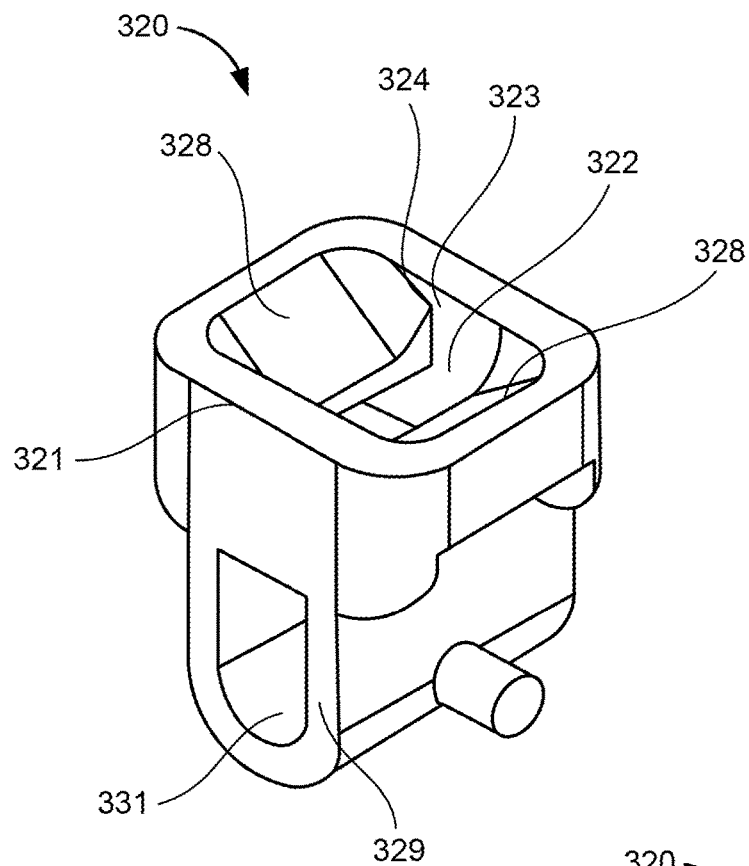
FIG. 3A is a perspective view of a catch according to an embodiment of the invention.
Figure 3B:
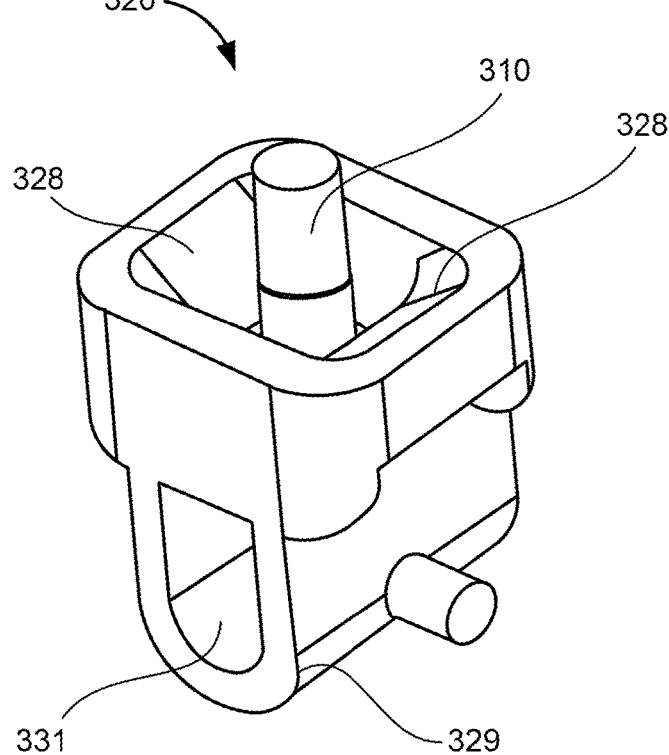
FIG. 3B is a perspective view of the catch of FIG. 3A coupled to a needle.

FIG. 3A is a perspective view of a catch 320 according to an embodiment of the invention. FIG. 3B is a perspective view of the catch 320 coupled to a needle 310. The catch 320 includes a receiving portion 321. Specifically, the catch 320 defines a cavity 322 and an opening 323 in communication with the cavity 322. As best illustrated in FIG. 3B, the receiving portion 321 is configured to receive the needle 310 such that the needle 310 is received into the cavity 322 through the opening 323.

In the illustrated embodiment, the catch 320 includes a sidewall 324 that defines the cavity 322. The catch 320 also includes projection members or flaps 328 that extend from the sidewall 324 into the cavity 322. The projection members or flaps 328 are configured to flex or bend when the needle 310 is inserted into the cavity 322 via the opening 323. As the projection members or flaps 328 flex or bend the needle 310 can be more fully received or inserted into the cavity 322. In some embodiments, the needle 310 includes an extended portion, a projection or rib. Once the rib or extended portion of the needle passes the projection members or flaps 328 (while the projection members or flaps 328 are in their flexed or bent configuration), the projection members 328 will return to their unflexed configuration thereby capturing the needle within the cavity or coupling the needle 310 to the catch 320 (as best illustrated in FIG. 3B). Accordingly, the needle 310 is configured to be moved into the catch 320 in one direction, but is retained within the cavity 322 and prevented from moving in an opposite direction.

In the illustrated embodiment, the needle 310 includes a tissue piercing portion. As best illustrated in FIG. 3B, the catch 320 is configured to couple to the needle 310 such that the tissue piercing portion of the needle 310 is disposed within the cavity 322 defined by the catch 320. In other words, the distal end portion or the tissue piercing portion of the needle 310 does not extend from the catch 320.

In the illustrated embodiment, the catch 320 includes a base portion 326. The base portion 326 includes a U-shaped member 329. The base portion 326 of the catch 320 provides a surface 331 to contact or otherwise help prevent the tissue piercing portion of the needle 310 from being over inserted into the catch 320 or from extending from the catch 320.

In some embodiments, the projection members 328 are configured to help facilitate the guiding of the needle 310 into the cavity 322 of the catch 320. Specifically, in the illustrated embodiment, the projection members 328 are sloped or angled. As the needle 310 enters the cavity 322 and the needle 310 contacts the projection members 328, the needle 310 will be guided or forced towards the center of the cavity 322.

Figure 4:
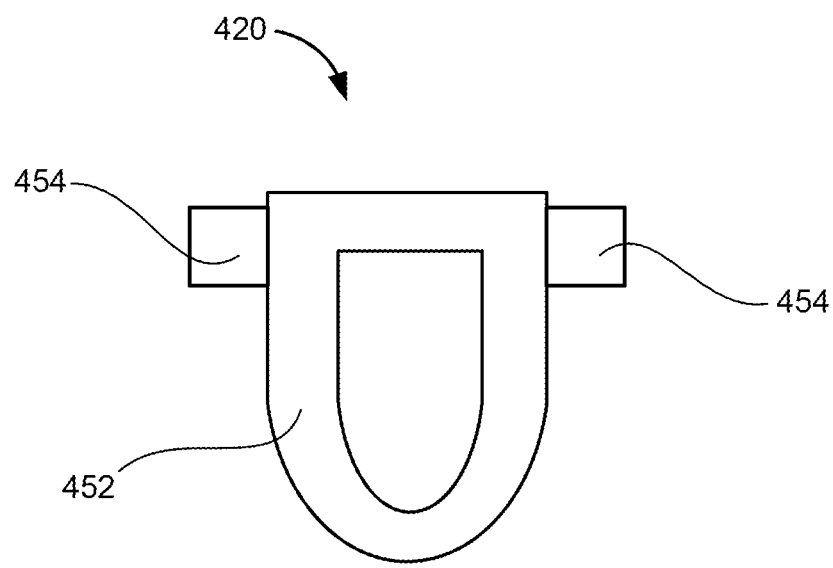
FIGS. 4-6 are side views of catches according to embodiments of the invention.
Figure 5:
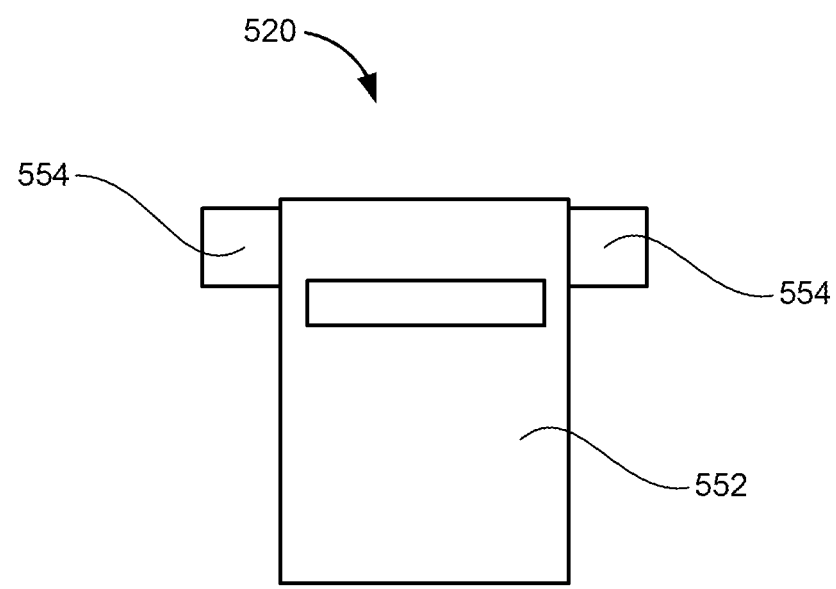
Figure 6:
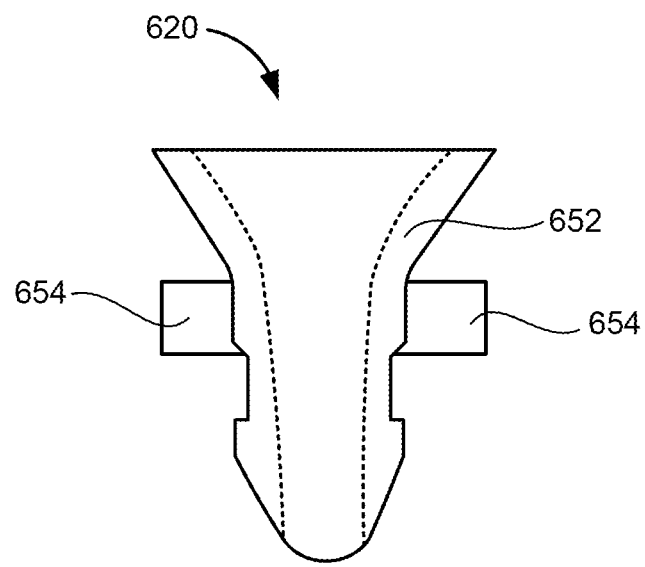

FIGS. 4-6 are side views of catches according to other embodiments of the invention. The catches of FIGS. 4-6 include retention members that are configured to help retain the catches in position within the body of the patient. In the illustrated embodiments, the retention members extend from body portions or outer surfaces of the catches and are configured to engage bodily tissue to help retain the catches in a location within the body of the patient.

FIG. 4 is a side view of a catch 420 according to an embodiment of the invention. The catch 420 may be similar to the box type catch of FIGS. 3A and 3B. The catch 420 includes a body portion 452 and retention members 454. The retention members 454 are configured to engage bodily tissue when the catch 430 is disposed within the body of a patient to help secure the catch 420 within the body of the patient. In the illustrated embodiment, the retention members 454 and the body portion 452 form a T shape. While two retention members are illustrated, the catch may include any number of retention members. For example, the catch may include one, three, four or more retention members. In some embodiments, the catch includes a single retention member that forms a ring or extends annularly around the catch. The retention members 454 may extend from the outer surface of the body portion 452 of the catch 420 at any location. In the illustrated embodiment, the retention members 454 extend from a top or upper portion of the body portion. In other embodiments, the retention members 454 extend from a mid portion or lower portion of the body portion.

FIG. 5 is a side view of a catch 520 according to an embodiment of the invention. The catch 520 may be similar to the box type catch of FIGS. 3A and 3B. The catch 520 includes a body portion 552 and retention members 554. The retention members 554 are configured to engage bodily tissue when the catch 520 is disposed within the body of a patient to help secure the catch 520 within the body of the patient. In the illustrated embodiment, the retention members 554 and the body portion 552 form a T shape. While two retention members are illustrated, the catch may include any number of retention members. For example, the catch may include one, three, four or more retention members. In some embodiments, the catch includes a single retention member that forms a ring or extends annularly around the catch. The retention members 554 may extend from the outer surface of the body portion 552 of the catch 520 at any location. In the illustrated embodiment, the retention members 554 extend from a top or upper portion of the body portion. In other embodiments, the retention members 554 extend from a mid portion or lower portion of the body portion.

FIG. 6 is a side view of a catch 620 according to an embodiment of the invention. The catch 620 may be similar to the funnel type catch of FIGS. 2A and 2B. The catch 620 includes a body portion 652 and retention members 654. The retention members 654 are configured to engage bodily tissue when the catch 620 is disposed within the body of a patient to help secure the catch 620 within the body of the patient. While two retention members are illustrated, the catch may include any number of retention members. For example, the catch may include one, three, four or more retention members. In some embodiments, the catch includes a single retention member that forms a ring or extends annularly around the catch. The retention members 654 may extend from the outer surface of the body portion 652 of the catch 620 at any location. In the illustrated embodiment, the retention members 654 extend from a middle portion of the body portion 652. In other embodiments, the retention members 654 extend from an upper portion or lower portion of the body portion.

Figure 7:
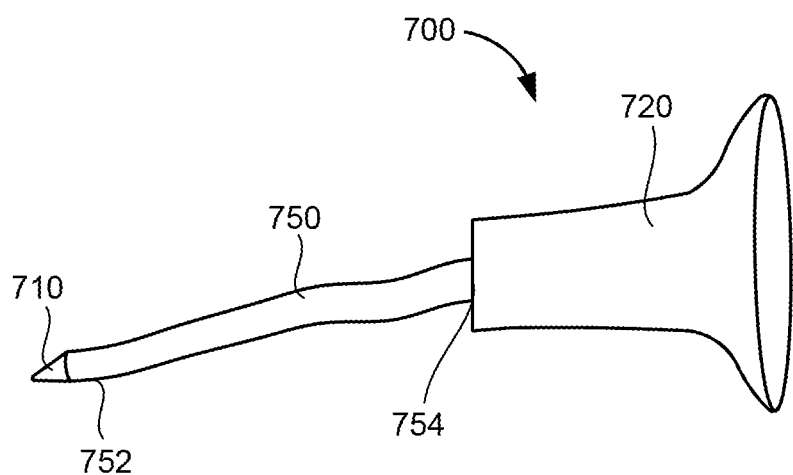
FIGS. 7 and 8 are perspective view of devices according to embodiments of the invention.
Figure 8:
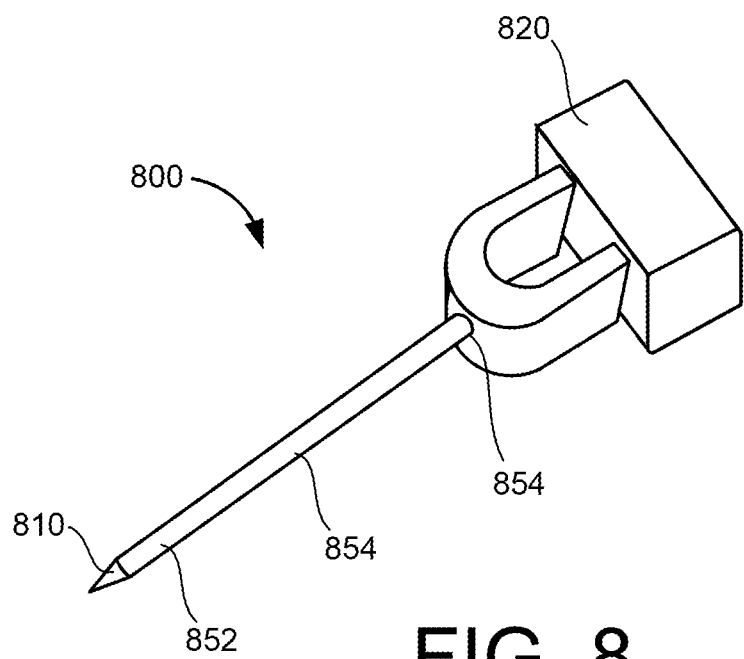

FIGS. 7 and 8 are perspective views of devices according to embodiments of the invention. FIG. 7 illustrates a medical device 700. The device 700 includes a needle 710, a catch 720, and a coupling member 750. The coupling member 750 includes a first end portion 752 that is coupled to the needle 710 and a second end portion 754 that is coupled to the catch 720.

The coupling member 750 may be any sort of elongate or other type of member. In some embodiments, the coupling member 750 is a filament or suture. In other embodiments, the coupling member 750 is another type of elongated member. Any known method may be used to couple the coupling member 750 to the needle 710 and the catch 720. For example, the coupling member 750 may be tied, glued, or molded to the catch 720 and to the needle 710. In other embodiments, another method of coupling may be used to couple the coupling member to the needle and to the catch.

In some embodiments, as illustrated in FIG. 7, the catch 720 may be a funnel type catch as illustrated in FIGS. 2A and 2B. In other embodiments, the catch 720 may be another type of catch.

In some embodiments, the needle or needle member 710 may include a tissue piercing portion 712. In the illustrated embodiment, the tissue piercing portion 712 is disposed opposite the portion of the needle 710 to which the coupling member 750 is coupled.

FIG. 8 illustrates a medical device 800. The device 800 includes a needle 810, a catch 820, and a coupling member 850. The coupling member 850 includes a first end portion 852 that is coupled to the needle 810 and a second end portion 854 that is coupled to the catch 820.

The coupling member 850 may be any sort of elongate or other type of member. In some embodiments, the coupling member 850 is a filament or suture. In other embodiments, the coupling member 850 is another type of elongated member. Any known method may be used to couple the coupling member 850 to the needle 810 and the catch 820. For example, the coupling member 850 may be tied, glued, or molded to the catch 820 and to the needle 810. In other embodiments, another method of coupling may be used to couple the coupling member to the needle and to the catch.

In some embodiments, as illustrated in FIG. 8, the catch 820 may be a box type catch as illustrated in FIGS. 3A and 3B. In other embodiments, the catch 820 may be another type of catch.

In some embodiments, the needle or needle member 810 may include a sharp or tissue piercing portion 812. In the illustrated embodiment, the tissue piercing portion 812 is disposed opposite the portion of the needle 810 to which the coupling member 850 is coupled.

Figure 9:
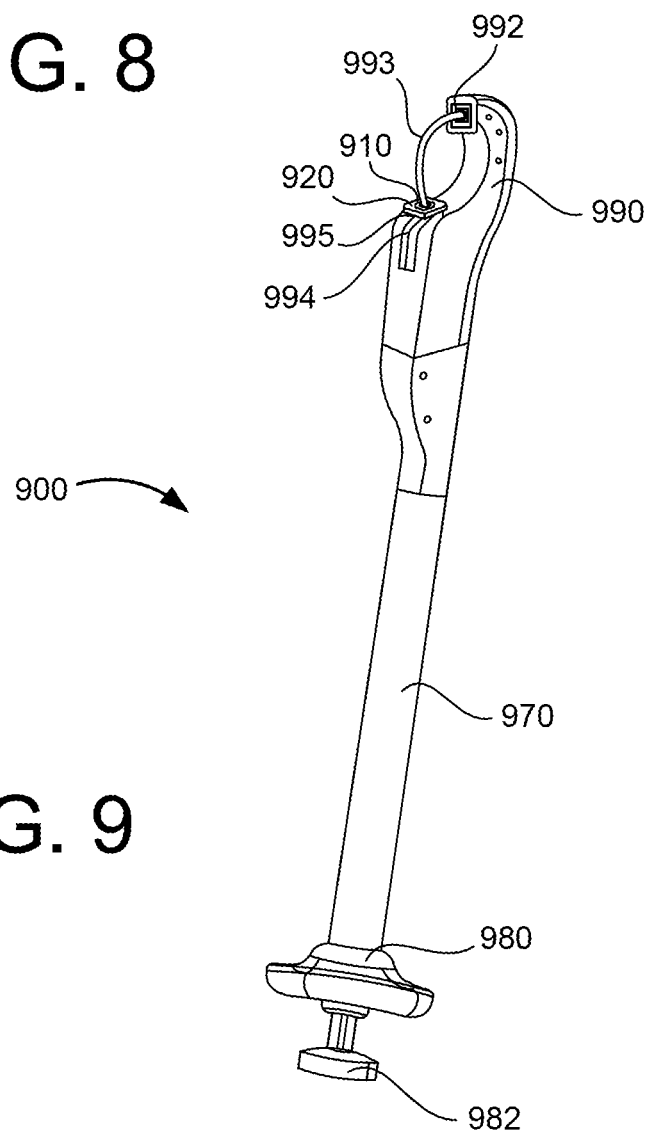
FIG. 9 is a perspective view of a delivery tool according to an embodiment of the invention.

FIG. 9 is a perspective view of a delivery device or tool 900 in accordance with an embodiment of the invention. The delivery device or tool 900 may be used to help secure an implant within a body of a patient. The delivery device or tool 900 includes an elongate portion 970, a proximal portion 980, and a distal portion 990.

The distal portion 990 of the delivery device 900 includes a first portion 992 configured to be removably coupled to a needle and a second portion 994 configured to be removably coupled to a catch. Specifically, in the illustrated embodiment, the distal portion 930 of the delivery device 900 includes a carrier 993 configured to be removably coupled to the needle. The distal portion also includes a nest 995 that is configured to be removably coupled to the catch.

Figure 10:
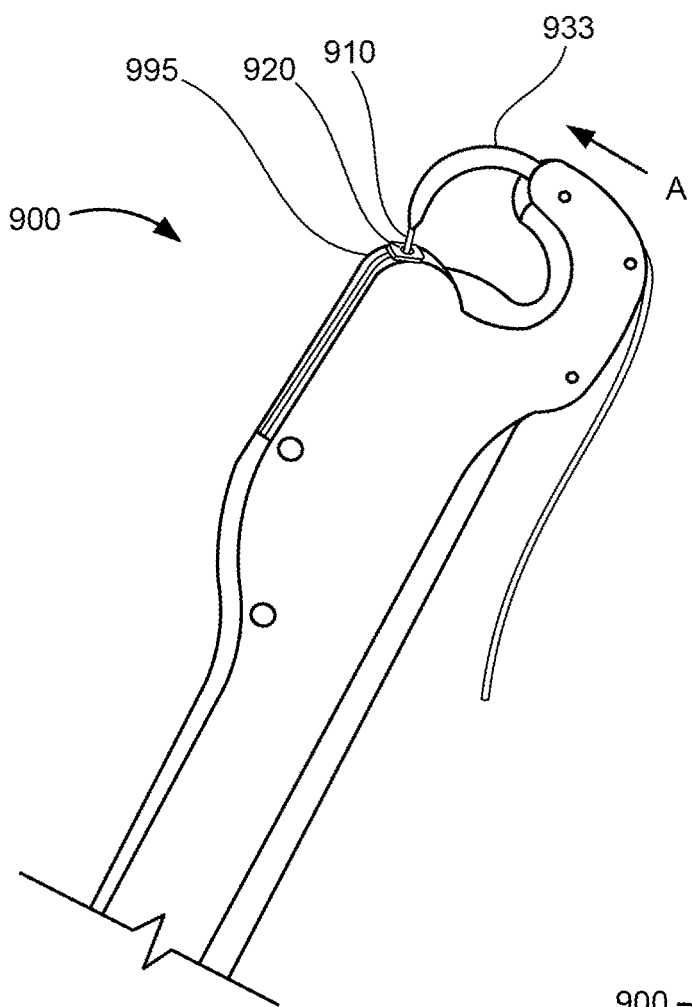
FIGS. 10-12 are perspective views of distal end portions of delivery tools according to embodiments of the invention.

As best illustrated in FIG. 10, the carrier 993 is configured to move the needle 910 towards and into the catch 920. In the illustrated embodiment, the carrier 993 is configured to move the needle 910 in a curved path and in a proximal direction (for example, along arrow A) towards and into the catch 920. In other embodiments, the carrier may be configured to move the needle in or along a linear path. In other embodiments, the carrier may be configured to move the needle in a distal direction.

In some embodiments, the carrier 993 includes a slot or opening that is configured to receive part of the needle 910 to removably couple the needle 910 to the carrier 993. Once the carrier has moved the needle 910 into the catch 920, the needle 910 will be coupled to the catch 920 and the carrier 993 can be retracted leaving the needle 910 coupled to the catch 920.

In the illustrated embodiment, the proximal portion 980 of the delivery tool 900 includes an actuator 982. The actuator 982 is operatively coupled to the carrier 993 and can be actuated or moved to move or cause the carrier 993 (and thereby move the needle 910 towards the catch 920). In some embodiments, the actuator 982 is linked to or operatively coupled to the carrier via linages. In some embodiments, the linkages are disposed within a lumen defined by the delivery tool 900 (such as the elongate portion 970 of the delivery tool 900).

Figure 11:
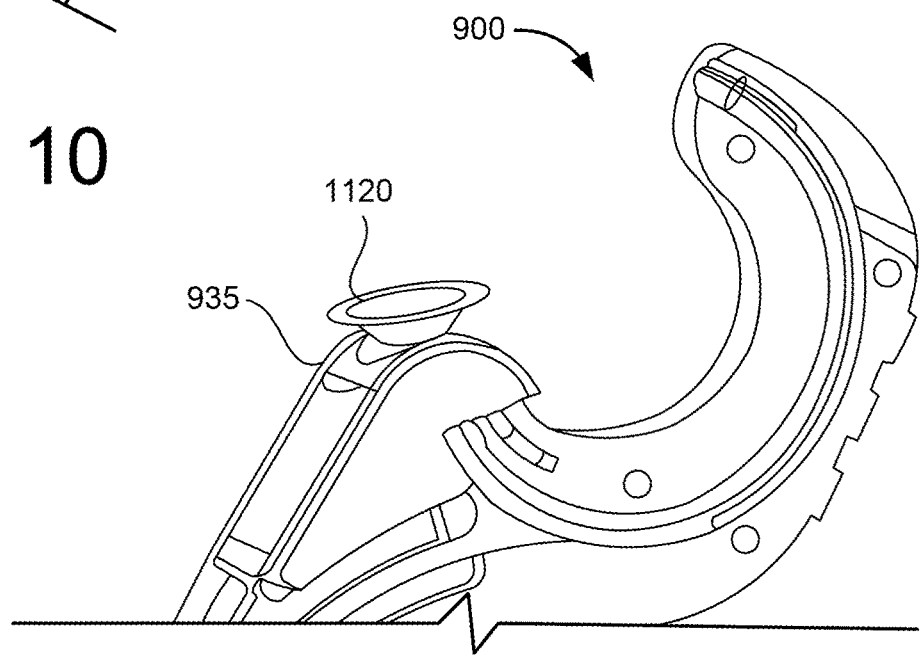
Figure 12:
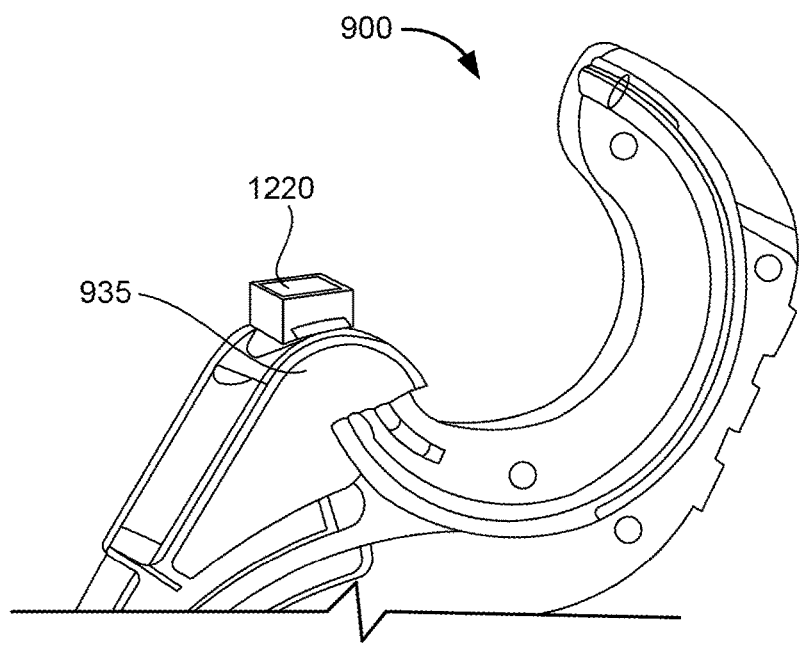

As illustrated in FIGS. 11 and 12, a funnel type catch 1120 or a box type catch 1220 may be coupled to the delivery device 900. Specifically, the catches 1120 and 1220 may be coupled to the nest 995 of the delivery device 900. In some embodiment, the catches are removably coupled to the nest 995. For example in some embodiments, the nest 935 may be configured to frictionally couple the catch. Thus, when enough force is placed on the delivery device 900 (for example, to remove the delivery device 900 from a body of a patient), the catch would be removed from the nest 995. In other embodiments, other mechanisms may be used to removably couple the catch to the nest 995.

Figure 13:
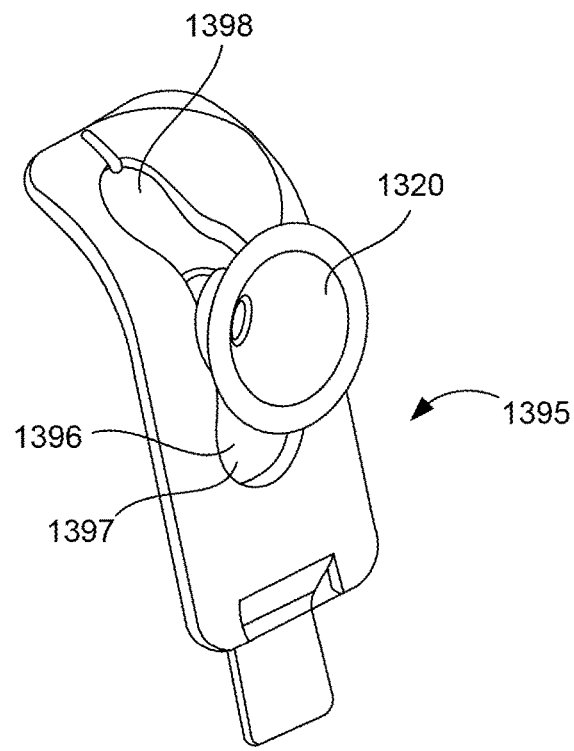
FIG. 13 is a perspective view of a portion of a delivery tool according to an embodiment of the invention.

FIG. 13 illustrates a nest 1395 that is configured to removably couple a catch (such as catch 1320) to the delivery device. For example, the nest 1395 is fixedly coupled to the delivery device (for example at a location at the distal end of the delivery device). The nest 1395 includes or defines a slot 1396. The slot 1396 includes a wide portion 1397 and a narrow portion 1398. The slot 1396 is configured to receive the catch 1320 through the wide portion 1397. The catch 1320 may then be moved or slide with respect to the nest 1395 to the narrow portion 1398 to couple the catch 1320 to the nest 1395. In some embodiments, the catch 1320 includes a projection that is configured to engage a portion of the narrow portion 1398 of the slot 1396 to couple or help couple the catch 1320 to the nest 1395 (or help prevent the catch 1320 from being removed from the slot 1396 at the narrow portion 1397).

Accordingly, the catch 1320 may be loaded into the nest 1395 by inserting the catch 1320 into the slot 1396 at the wide portion 1397 of the slot 1396 and moved to the narrow portion 1398 of the slot 1396. The catch 1320 can then be removed from the nest 1395 (for example, after the needle has been coupled to the catch) by moving or sliding the catch 1320 back to the wide portion 1397 of the slot 1396 and removing the catch 1320 from the slot 1396.

Figure 14:
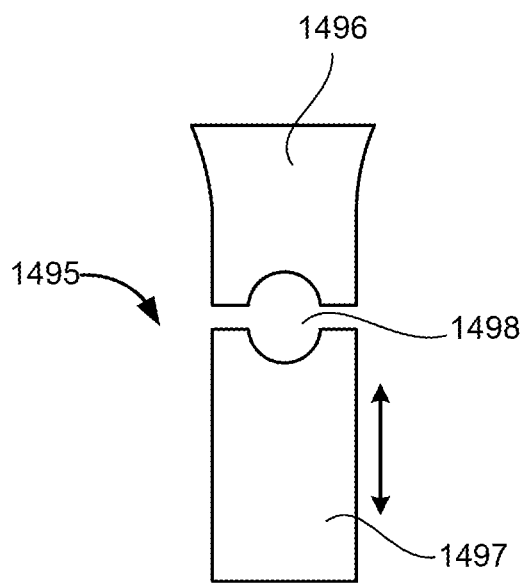
FIG. 14 is a perspective view of a portion of a delivery tool according to an embodiment of the invention.
Figure 15:
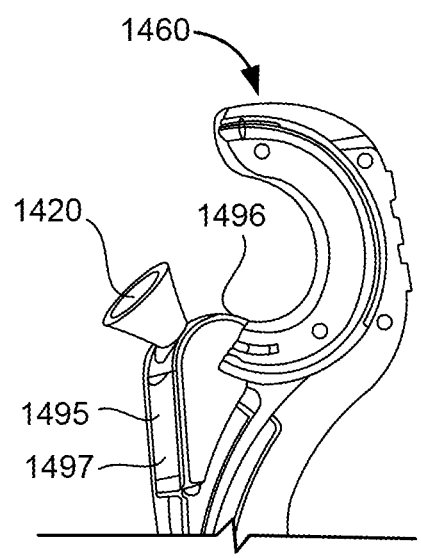
FIGS. 15-16 are perspective views of a distal end portion of a delivery tool according to an embodiment of the invention.
Figure 16:
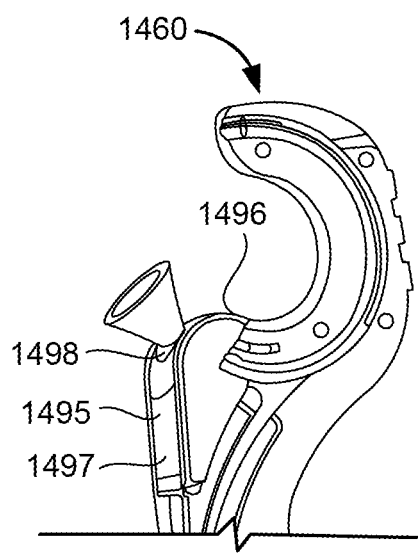

FIG. 14 is a perspective view of a nest 1495 according to an embodiment of the invention. FIGS. 15 and 16 are perspective views of a distal portion of a delivery tool 1460 that includes the nest 1495. The nest 1495 includes a first portion 1496 and a second portion 1497. The second portion 1497 is configured to move with respect to the first portion 1496. For example, in some embodiments, the second portion 1497 may be configured to move with respect to the first portion 1496 by actuating a lever or actuator that is operatively connected or coupled to the second portion 1497. In some embodiments, the lever or actuator may be coupled to or disposed at a proximal end portion of the delivery device 1460.

The first portion 1496 and the second portion 1497 collectively define an opening 1498. Specifically, in the illustrated embodiment, the first portion 1496 includes an edge that has a concave or curved portion. Similarly, the second portion 1497 includes an edge that has a concave or curved portion. The concave or curved portions collectively define the opening 1498.

In the illustrated embodiment, the opening 1498 is disposed between the first portion 1496 and the second portion 1497. As the second portion 1497 is configured to move with respect to the first portion 1496, the second portion 1497 can be moved to enlarge the opening 1498 or make the opening 1498 smaller. For example, the second portion 1497 may be moved to an open position or configuration, as illustrated in FIG. 16, to make the opening 1498 or space between the first portion 1496 and the second portion 1497 large. In this configuration, the catch 1420 may be inserted into the opening 1498. The second portion 1497 may then be moved to a closed position or configuration, as illustrated in FIG. 15, to make the opening 1498 smaller. In this configuration, the first portion 1496 and the second portion 1497 collectively help retain the catch 1420 in place. In some embodiments, the first portion 1496 and the second portion 1497 frictionally couple the catch 1420 in place. In other embodiments, the first portion 1496 and the second portion 1497 surround or grasp a portion of the catch 1420 to couple the catch 1420 to the device 1460. The second portion 1497 may then be moved to the first or open position (as illustrated in FIG. 16) to release the catch 1420 from the device 1460.

Figure 17:
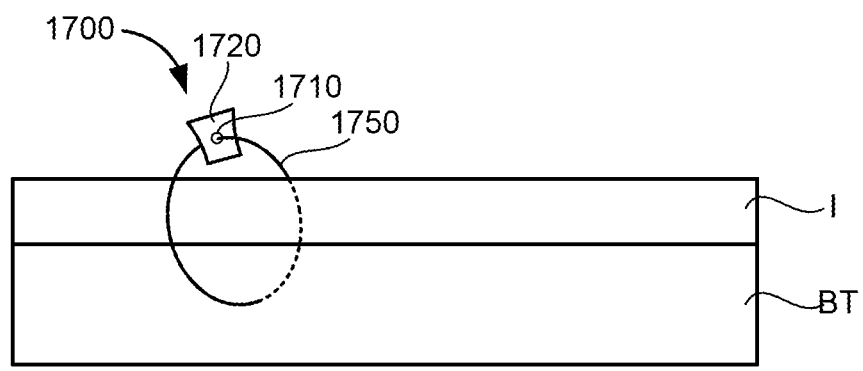
FIG. 17 is a schematic view of a device disposed within a body of a patient.

FIG. 17 is a schematic side or cross-sectional view of a medical device 1700 disposed within a body of a patient. The medical device 1700 includes a needle 1710, a catch 1720 and a coupling member or filament 1750. The medical device 1700 is configured to help hold or retain an implant I in place within the body of the patient. Specifically, the medical device 1700 forms a loop or a circle and extends through the implant I and bodily tissue BT. The loop or circle of the medical device helps retain or hold the implant I adjacent or coupled to the bodily tissue BT.

The implant I may be any type of bodily implant. In some embodiment, the implant I is formed of biocompatible material. For example, in some embodiments, the implant I is a woven or mesh material. The implant I may have any shape. For example, the implant I may be rectangular, circular, square, or any other shape. The implant I may have a body portion and extension portions that extend from the body portion.

In the illustrated embodiment, only one medical device 1700 is used to couple the implant I to the bodily tissue. In other embodiments, more than one medical device may be used to couple the implant I to the bodily tissue. For example, in some embodiments, a plurality of medical devices are used at different locations along the implant I to couple the implant to the bodily tissue BT.

Figure 18:
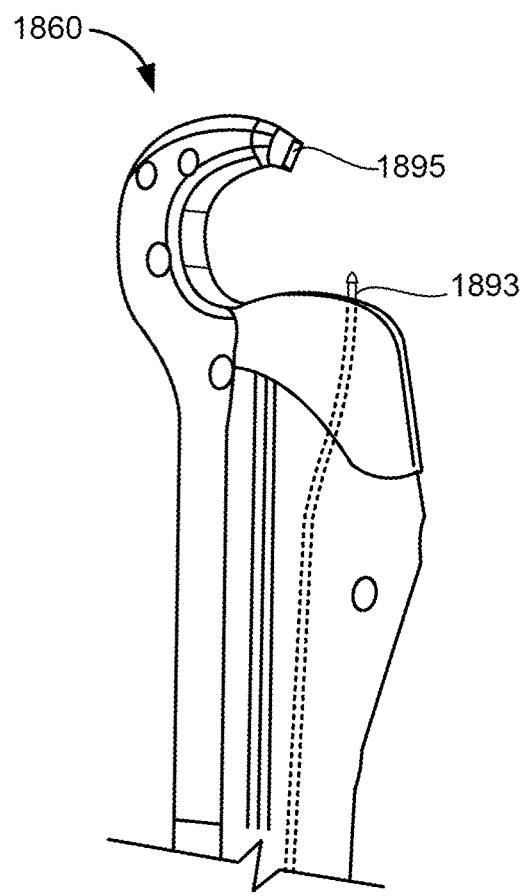
FIGS. 18-19 are side views of a distal end portion of a delivery tool according to an embodiment of the invention.
Figure 19:
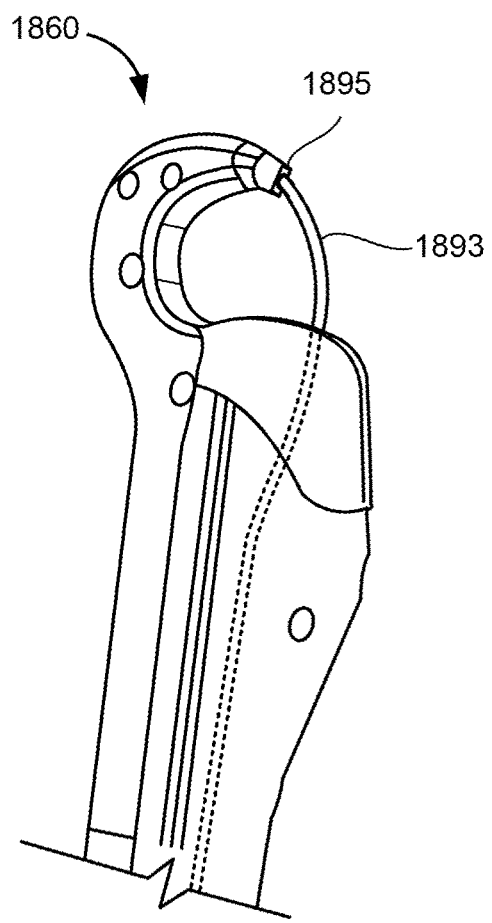

FIGS. 18 and 19 are side views of a distal end portion of a delivery device 1860 according to an embodiment of the invention. In this embodiment, the nest 1895 (which is configured to be coupled to a catch) is disposed distally of the carrier 1893 (which is configured to be coupled to a needle). The carrier 1893 is configured to move the needle distally towards the catch from a first position (as illustrated in FIG. 18) to a second position (as illustrated in FIG. 19). In the illustrated embodiment, the carrier 1893 is configured to move the needle in a curved or non-linear path.

Figure 20:
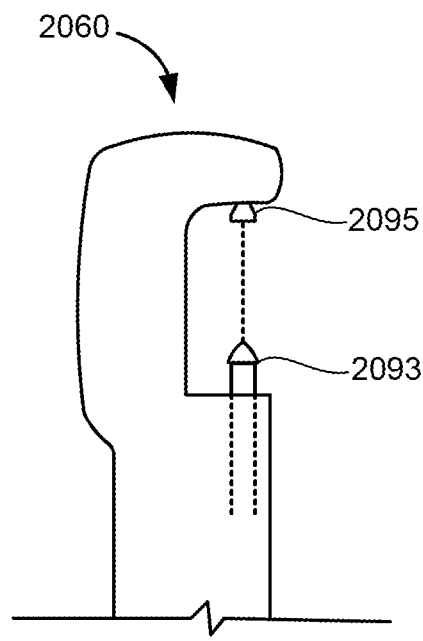
FIGS. 20-23 are side views of distal end portions of delivery tools according to embodiments of the invention.

FIGS. 20-23 are side views of distal end portions of delivery tools according to embodiments of the invention. FIG. 20 illustrates a distal end portion of delivery tool 2060. In this embodiment, the nest 2095 (which is configured to be coupled to a catch) is disposed distally of the carrier 2093 (which is configured to be coupled to a needle). The carrier 2093 is configured to move the needle distally towards the catch from a first position to a second position. In the illustrated embodiment, the carrier 2093 is configured to move the needle in a substantially linear path.

Figure 21:
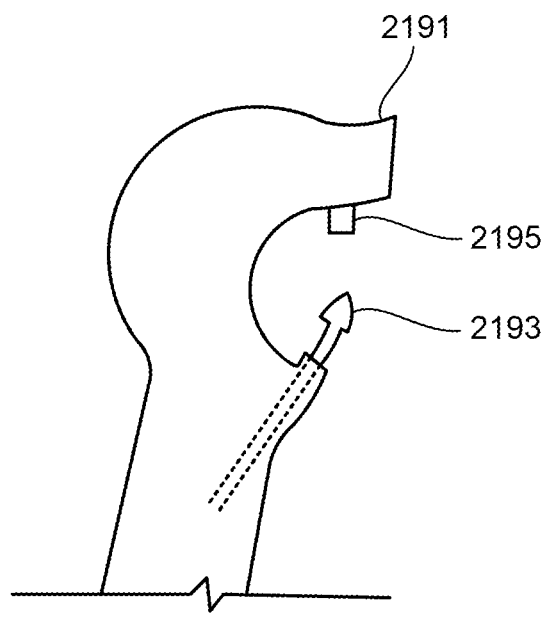

FIG. 21 illustrates a distal end portion of delivery tool 2160. In this embodiment, the nest 2195 (which is configured to be coupled to a catch) is disposed distally of the carrier 2193 (which is configured to be coupled to a needle). The carrier 2193 is configured to move the needle distally towards the catch. In the illustrated embodiment, the distal end portion of the delivery tool 2160 includes a guard member or portion 2191. The guard member or portion 2191 is configured to contact bodily tissue when the tool 2160 is disposed within the body of a patient to help prevent unwanted or too much bodily tissue from entering into the opening of the tool 2160 and allowing too much bodily tissue from being in the pathway of the needle.

Figure 22:
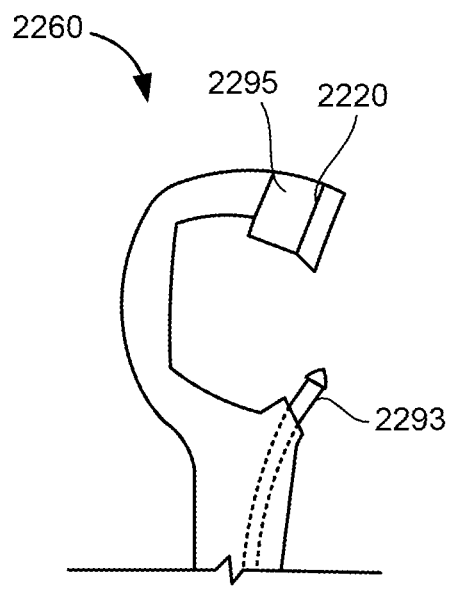

FIG. 22 illustrates a distal end portion of delivery tool 2260. In this embodiment, the nest 2295 (which is configured to be coupled to a catch) is disposed distally of the carrier 2293 (which is configured to be coupled to a needle). The carrier 2293 is configured to move the needle distally towards the catch. In the illustrated embodiment, the nest 2295 is configured to receive a portion of the catch 2220 to removably couple the catch 2220 to the tool 2260. For example, in some embodiments, the nest 2295 includes a hook portion that is configured to removably couple the catch 2220 to the nest 2295.

Figure 23:
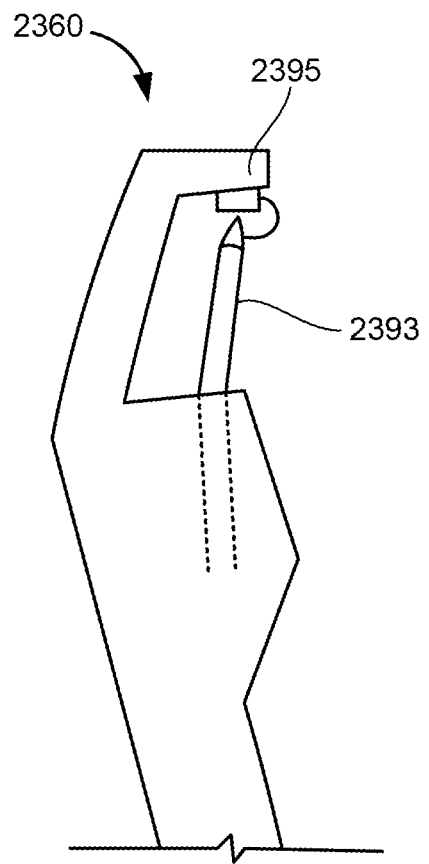

FIG. 23 illustrates a distal end portion of delivery tool 2360. In this embodiment, the nest 2395 (which is configured to be coupled to a catch) is disposed distally of the carrier 2393 (which is configured to be coupled to a needle). The carrier 2393 is configured to move the needle distally towards the catch. In the illustrated embodiment, the carrier 2393 is configured to move the needle along a linear path at an angle (non-parallel) with respect to a longitudinal axis of the delivery tool 2360.

Figure 24:
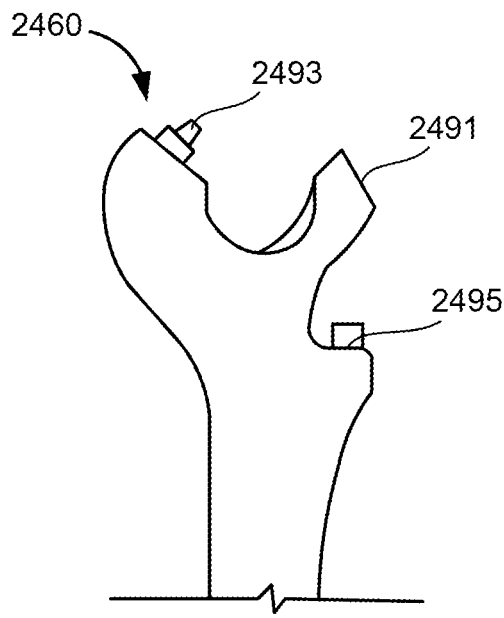
FIGS. 24-25 are side views of a distal end portion of a delivery tool according to an embodiment of the invention.
Figure 25:
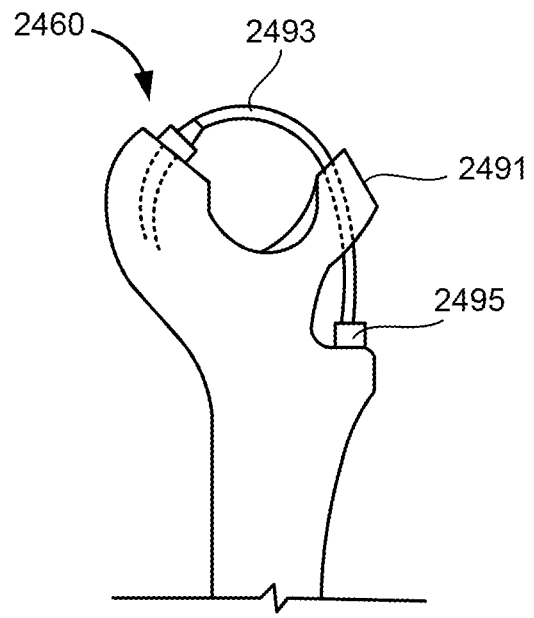

FIGS. 24-25 are side views of a distal end portion of a delivery tool 2460 according to an embodiment of the invention. In this embodiment, the nest 2495 (which is configured to be coupled to a catch) is disposed proximally of the carrier 2493 (which is configured to be coupled to a needle). The carrier 2493 is configured to move the needle proximally towards the catch. In the illustrated embodiment, the distal end portion of the delivery tool 2460 includes a guard member or portion 2491. The guard member or portion 2491 is configured to contact bodily tissue when the tool 2460 is disposed within the body of a patient to help prevent unwanted or too much bodily tissue from entering into the opening of the tool 2460 and allowing too much bodily tissue from being in the pathway of the needle. In some embodiments, the carrier 2493 (and the needle) are configured to pass around the guard member or portion 2491. In other embodiments, the guard member or portion 2491 may include or define a slot, a channel, or a lumen (for example, a slot 2492 is illustrated in FIG. 25). In such embodiments, the carrier 2493 is configured to pass through the slot, channel, or lumen.

Figure 26:
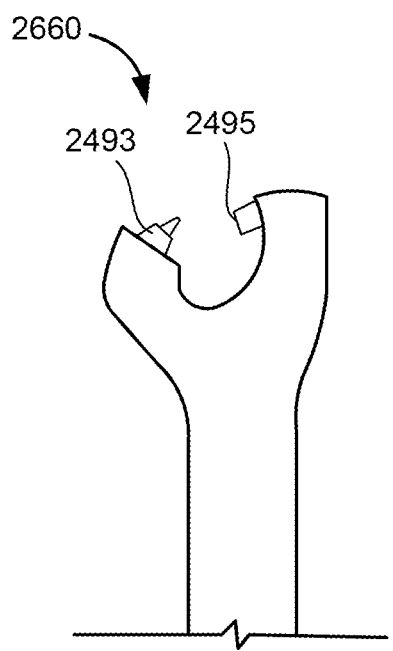
FIGS. 26-27 are side views of a distal end portion of a delivery tool according to an embodiment of the invention.
Figure 27:
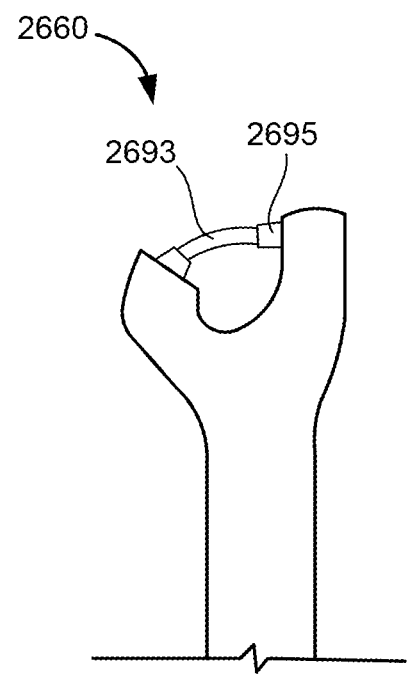

FIGS. 26 and 27 are side views of a distal end portion of a delivery device 2660 according to an embodiment of the invention. In this embodiment, the nest 2695 (which is configured to be coupled to a catch) is disposed at one side of a distal most end or tip portion of the delivery device 2260. The carrier 2693 (which is configured to be coupled to a needle) is disposed at another side of the distal most end or tip portion of the delivery device 2260. The carrier 2693 is configured to move the needle towards the catch from a first position (as illustrated in FIG. 26) to a second position (as illustrated in FIG. 27). In the illustrated embodiment, the carrier 2693 is configured to pass the needle through tissue that is disposed distally of the delivery tool 2660 (rather than to a side of the delivery tool 2660).

Figure 28:
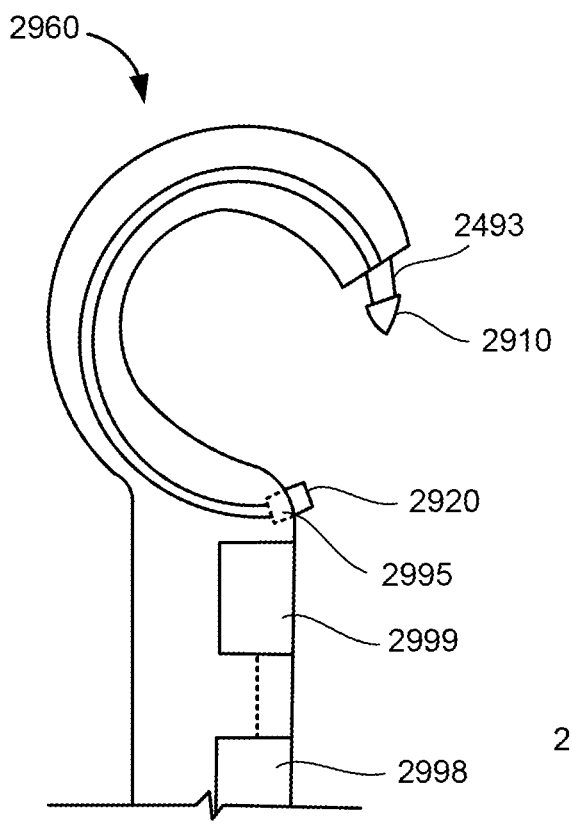
FIGS. 28-29 are side views of a distal end portion of a delivery tool according to an embodiment of the invention.
Figure 29:
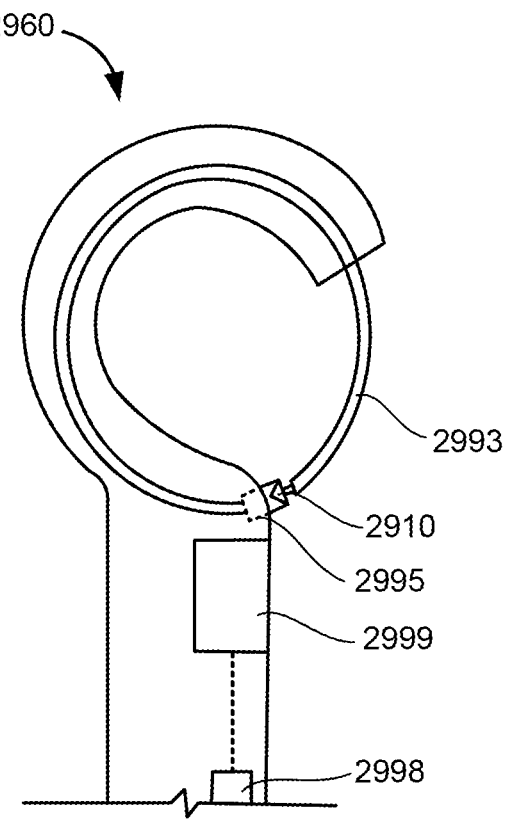

FIGS. 28 and 29 are side views of a distal end portion of a delivery device 2960 according to an embodiment of the invention. In this embodiment, the nest 2995 (which is configured to be coupled to a catch) is disposed proximally of the carrier 2993 (which is configured to be coupled to a needle). The carrier 2993 is configured to move the needle towards the catch from a first position (as illustrated in FIG. 28) to a second position (as illustrated in FIG. 28).

In the illustrated embodiment, the catch 2920 is configured to conform to the surface or surround the surface of the needle 2910 when the needle contacts the catch 2920. Specifically, in the illustrated embodiment, the catch 2920 is formed of a material that is configured to mold around the needle 2920. The material of the catch 2920 is configured to be heated and melt or form around the needle 2910 to couple the needle 2910 to the catch 2920. In the illustrated embodiment, the delivery tool 2960 includes a heat source 2999 that is configured to heat the material of the catch 2920 to melt the catch 2920 or otherwise allow the catch 2920 to shape or form around the needle 2910. The heat source 2999 may be any type of heat source and in the illustrated embodiment, the heat source 2999 is disposed adjacent the nest 2995 (or the catch 2920). In some embodiments, the heat source 2999 may be activated or caused to heat the catch 2920 via a switch 2998 that is operatively coupled to the heat source 2999. In such embodiments, the needle 2910 can be passed though bodily tissue and into the catch 2920. The catch 2920 can be heated to couple the catch 2920 to the needle 2910. The needle 2910 can then be released from the carrier 2993 and the catch 2920 can be released from the nest 2995.

Figure 30:
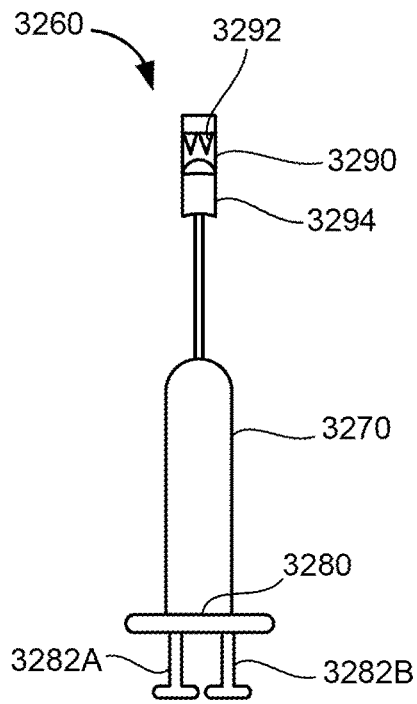
FIG. 30 is a side view of a delivery tool according to an embodiment of the invention.
Figure 31:
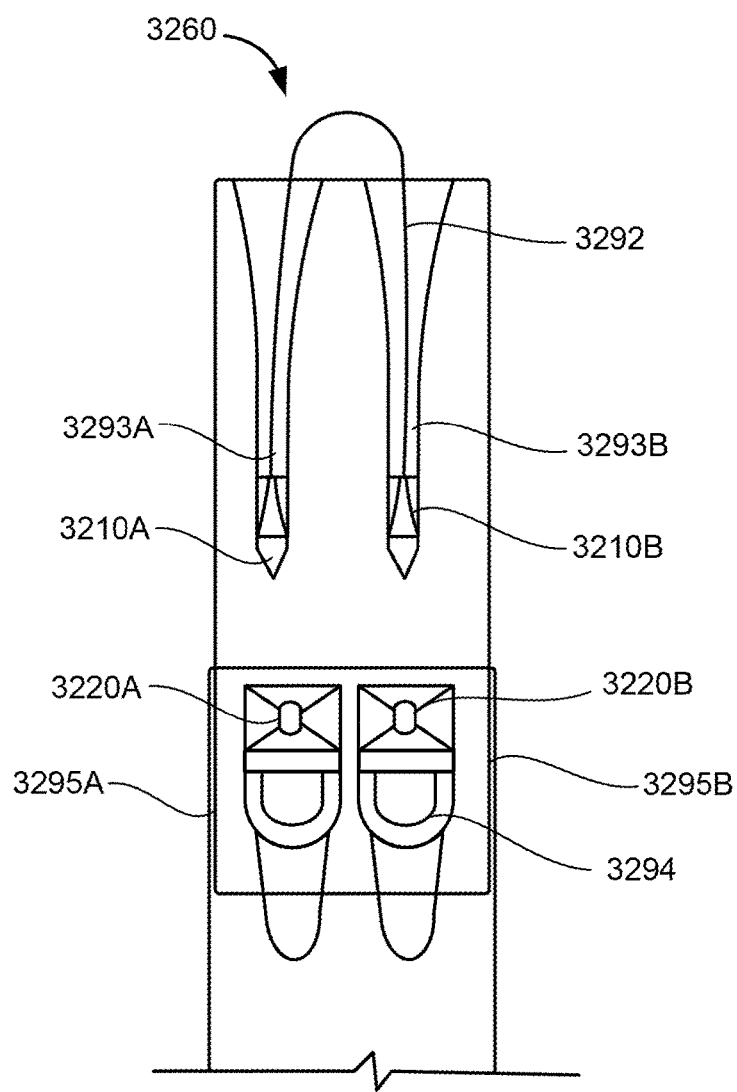
FIG. 31 is a side view of a distal end portion of the delivery tool of FIG. 30.
Figure 32:
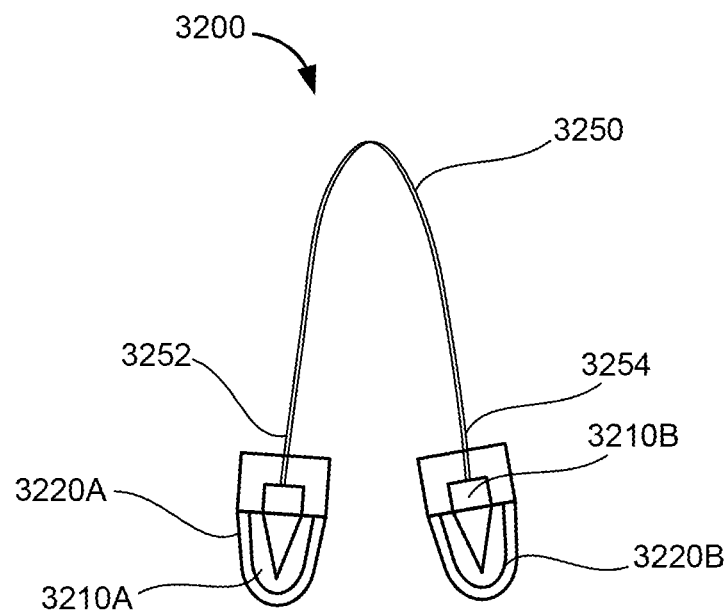
FIG. 32 is a side view of a device according to an embodiment of the invention.

FIG. 32 illustrates a medical device 3200 according to an embodiment of the invention. FIG. 30 is a side view of a delivery tool 3260 that is configured to deliver or place the medical device 3200 within a body of a patient. FIG. 31 is a side view of a distal end portion of the medical device 3200 coupled to the delivery tool 3260.

The medical device 3200 includes a first needle or needle member 3210A and a second needle or needle member 3210B. The needle members 3210A and 3210B are coupled or tethered together via a coupling member 3250. In the illustrated embodiment, the coupling member 3250 includes a first end portion 3252 coupled to the first needle 3210A and a second end portion 3254 coupled to the second needle 3210B.

The medical device 3200 also includes a first catch 3220A and a second catch 3220B. As illustrated, the first needle 3210A is configured to be coupled to the first catch 3220A. Similarly, the second needle 3210B is configured to be coupled to the second catch 3220B. The first catch 3220A and the second catch 3220B can be any type of catch member. For example, in the illustrated embodiment, the first catch 3220A and the second catch 3220B are structurally and functionally similar to the catch 320 of FIG. 3A. In other embodiments, the first catch 3220A and the second catch 3220B are different types of catches.

The delivery device 3260 is configured to place or dispose the medical device 3200 within a body of a patient. For example, the delivery device or tool 2360 may be used to help secure an implant within a body of a patient. The delivery device or tool 2360 includes an elongate portion 2370, a proximal portion 2680, and a distal portion 2390.

The distal portion 2390 of the delivery device 2360 includes a first portion 2392 that is configured to be removably coupled to a first needle (such as first needle 3210A as shown in FIG. 31) and to a second needle (such as second needle 3210B as shown in FIG. 31). Specifically, in the illustrated embodiment, the distal portion 3290 of the delivery device 3260 includes a first carrier 3293A configured to be removably coupled to the first needle 3210A and a second carrier 3293B configured to be removably coupled to the second needle 3210B.

The distal portion 2390 of the delivery device 3260 also includes a second portion 3294 that is configured to be removably coupled to a first catch (such as first catch 3220A as illustrated in FIG. 31) and to a second catch (such as second catch 3220B as illustrated in FIG. 31). Specifically, in the illustrated embodiment, the distal portion 3290 of the delivery device 3260 includes a first nest 3295A configured to be removably coupled to the first catch 3220A and a second nest 3295B configured to be removably coupled to the second catch 3220B.

The first carrier 3293A and the second carrier 3293B are configured to move the needles 3210A and 3210B towards and into the catches 3220A and 3220B. The carriers 3293A and 3290B may be configured to move the needles in a curved or linear path.

In some embodiments, the carriers 3293A and 3293B include slots or openings that are configured to receive portions of the needles 3210A and 3210B to removably couple the needles to the carriers. Once the carriers have moved the needles into the catches, the needles will be coupled to the catches and the carriers can be retracted leaving the needles coupled to the catches (the first needle 3210A being coupled to the first catch 3220A and the second needle 3210B being coupled to the second catch 3220B as illustrated in FIG. 32).

In the illustrated embodiment, the proximal portion 3280 of the delivery tool 3260 includes a first actuator 3282A and a second actuator 3282B. The actuators 3282A and 3282B are operatively coupled to the carriers 3293A and 3293B (the first actuator 3282A being operatively coupled to the first carrier 3293A and the second actuator 3282B being operatively coupled to the second carrier 3293B) and can be actuated or moved to move or cause the carriers 3293A and 3293B (and thereby move the needles 3210A and 3210B towards the catches 3220A and 3220B). In some embodiments, the actuators are linked to or operatively coupled to the carriers via linages. In some embodiments, the linkages are disposed within a lumen defined by the delivery tool 3260 (such as the elongate portion 3270 of the delivery tool 3260).

In the illustrated embodiment, the actuators 3282A and 3282B may be operated or actuated independently of each other. In other words, the first actuator 3282A may be actuated to move the first carrier 3293A and then later in time the second actuator 3282B may be actuated to move the second carrier 3293B. In some embodiments, the actuators may be actuated at the same time or simultaneously. In some embodiments, the delivery device includes a single actuator that is operatively coupled to both carriers. In such embodiments, actuation of the single actuator may cause the carriers to move at the same time or simultaneously.

Figure 33:
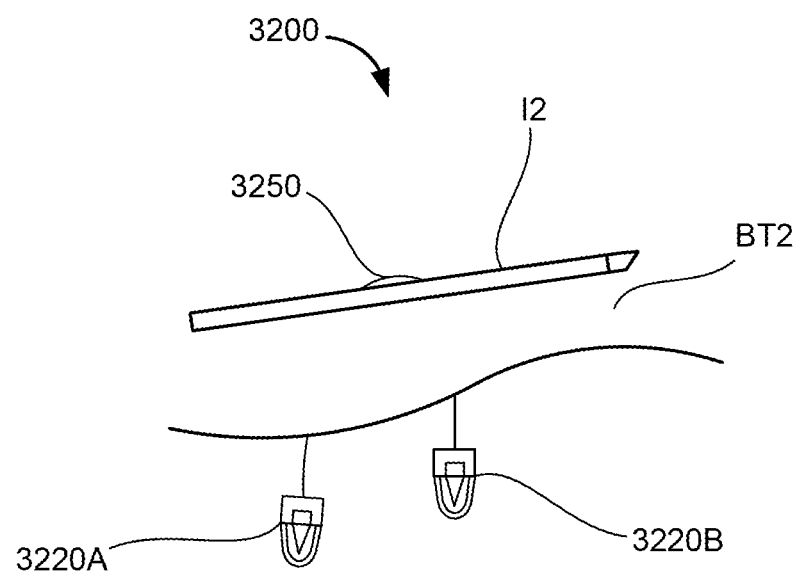
FIG. 33 is a schematic view of the device of FIG. 32 disposed within a body of a patient.

FIG. 33 is a schematic illustration of the medical device 3200 disposed within a body of a patient. Specifically, the medical device 3200 is passed though an implant I2 and through bodily tissue BT2 to help hold or retain the implant I2 coupled or adjacent to the bodily tissue BT2. One or more than one medical device 3200 may be used to couple the implant I2 to the bodily tissue BT2.

Figure 34:
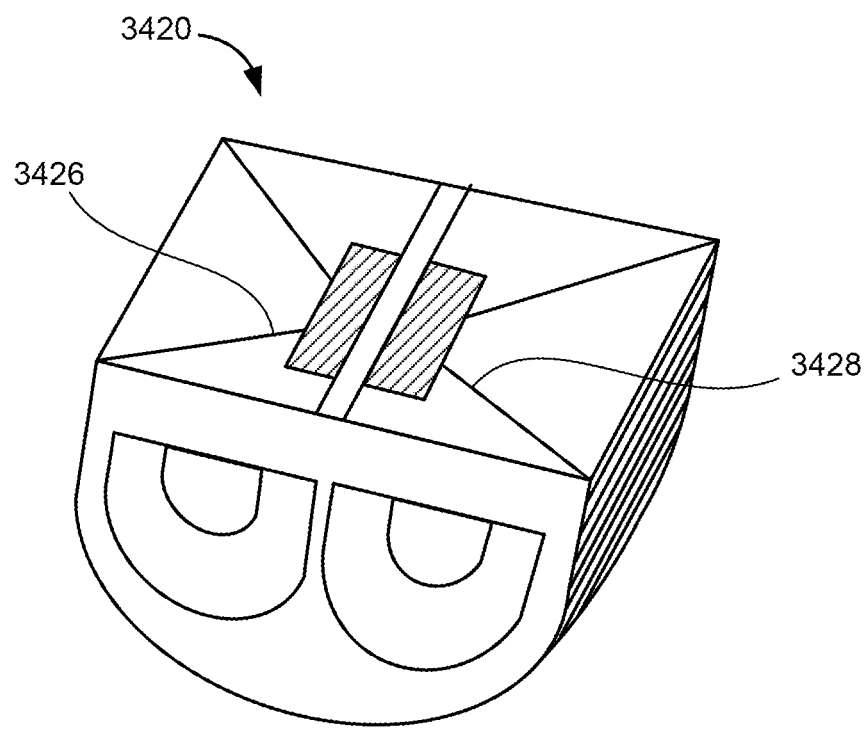
FIG. 34 is a perspective view of a catch according to an embodiment of the invention.

FIG. 34 is a perspective view of a catch 3420 according to an embodiment of the invention. In the illustrated embodiment, the catch 3420 includes a first portion 3426 configured to receive and couple to a first needle and a second portion 3428 configured to receive and couple to a second needle. In some embodiments, the catch 3420 may be used in place of catches 3420A and 3420B of the above embodiment.

In the illustrated embodiment, the first portion 3426 is disposed adjacent the second portion 3428. The first portion 3426 and the second portion 3428 may each be structurally and functionally similar to the catches described herein (such as the catches of FIGS. 2A and 3A).

Figure 35:
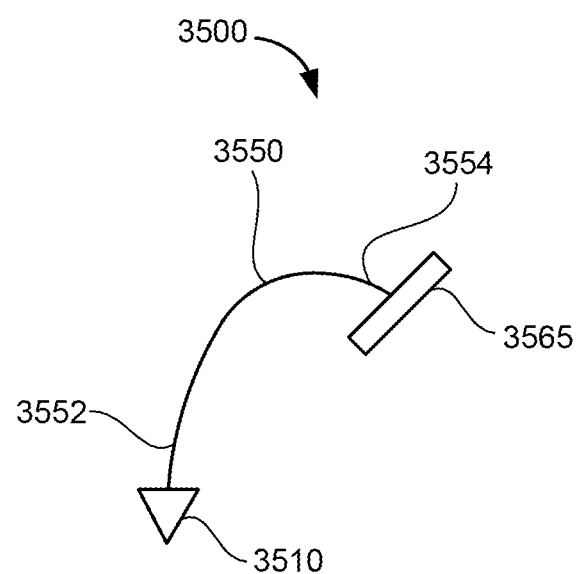
FIGS. 35-36 are perspective views of a device according to an embodiment of the invention.
Figure 36:
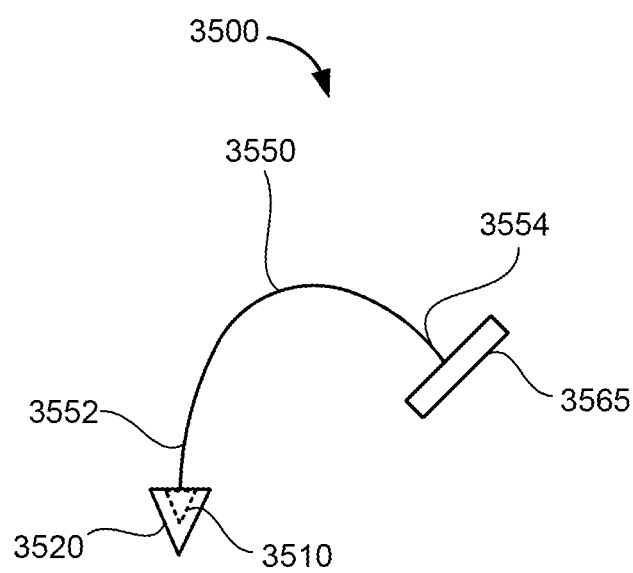

FIGS. 35 and 36 are perspective views of a medical device 3500 according to an embodiment of the invention. The medical device 3500 includes a needle 3510, a catch 3520, and a coupling member or filament 3550. The medical device also includes an anchor member 3565. The coupling member or filament 3550 is coupled to and extends from the needle 3510 to the anchor member 3565. In the illustrated embodiment, the coupling member 3550 includes a first end portion 3552 that is coupled to the needle 3510 and a second end portion 3554 that is coupled to the anchor member 3565. Any known method may be used to couple the coupling member 3550 to the needle 3510 and to the anchor 3565. For example, the coupling member 3550 may be tied, glued, or otherwise coupled to the needle 3510 and to the anchor 3565.

In the illustrated embodiment, the anchor 3565 has a linear shape. In other embodiments, the anchor 3565 has a different shape. For example, the anchor may have a non-linear shape, a T shape, an X shape, or any other shape.

The catch 3520 is configured to receive and couple to the needle 3510. The catch 3520 may be any type of catch mechanism. In some embodiments, the catch 3520 is structurally and functionally similar to the catches described herein.

The medical device 3500 may inserted or placed within a body of a patient using a delivery device or tool as described above. Specifically, the needle 3510 may be removably coupled to a carrier portion of the delivery device and the catch may be removably coupled to a nest portion of the delivery device. The needle may then be advanced towards the catch by the carrier. Once the needle is received by the catch the needle will be coupled to the catch and the needle and the catch can be removed from the delivery device.

Figure 37:
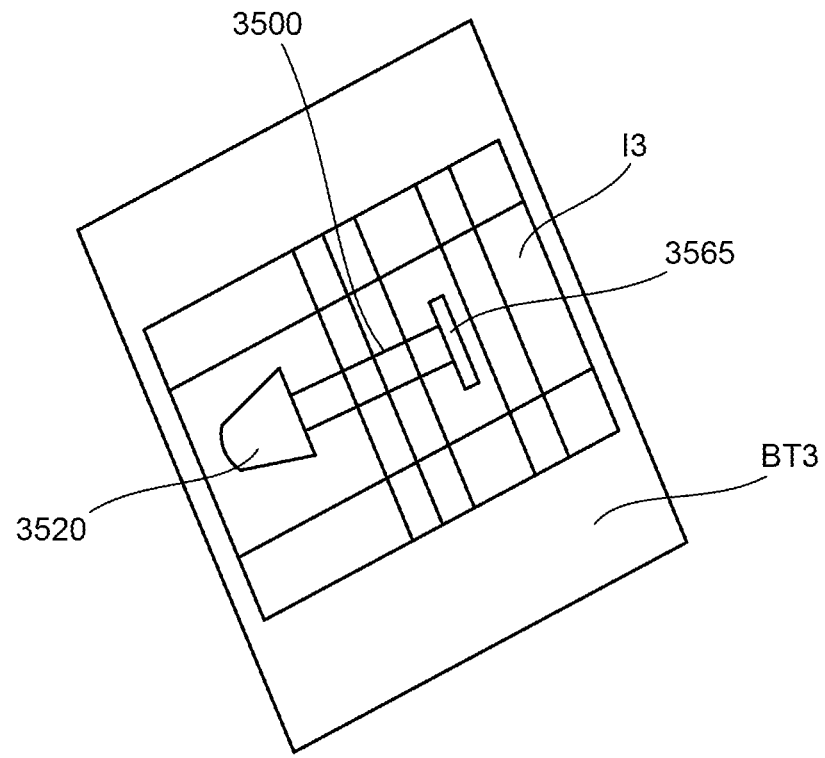
FIG. 37 is a schematic view of the device of FIGS. 35-36 disposed within a body of a patient according to an embodiment of the invention.

As schematically illustrated in FIG. 37, the medical device 3500 may be used to couple or attach an implant I3 within a body of a patient. As illustrated in FIG. 37, the medical device 3500 extends through a portion of an implant I3 and though bodily tissue BT3 to couple the implant I3 to the bodily tissue BT3. In the illustrated embodiment, the catch 3520 and the anchor member 3565 function to prevent or help prevent the medical device 3500 from pulling through or releasing from the implant I3 or the bodily tissue BT3. In the illustrated embodiment, the implant I3 is a mesh or woven implant. In other embodiments, the implant I3 is a different type of implant.

Figure 38:
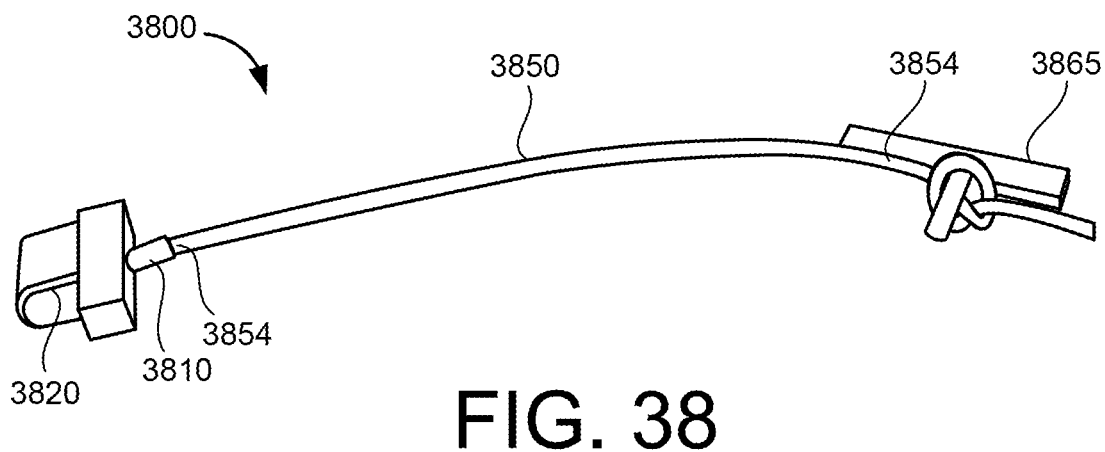
FIGS. 38-46 illustrate devices according to embodiments of the invention.
Figure 39:
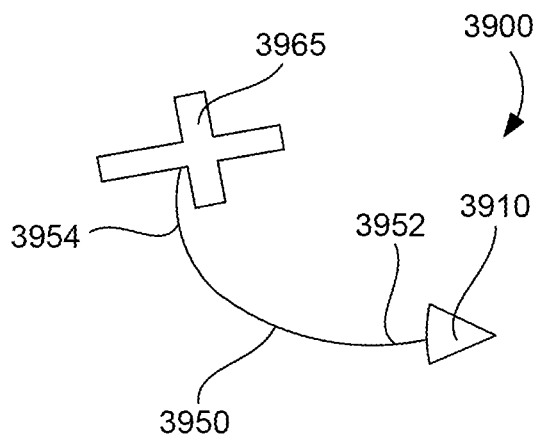
Figure 40:
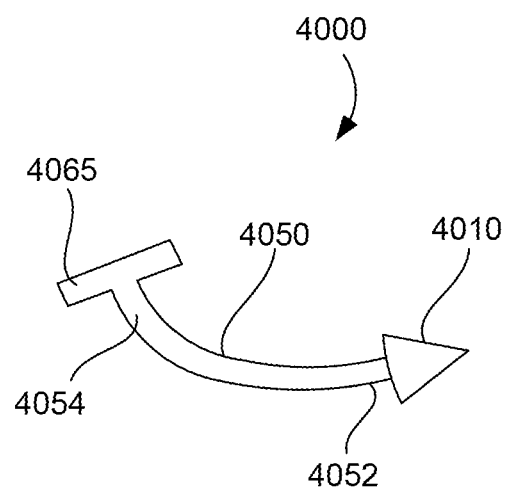

FIGS. 38-40 illustrate medical devices according to embodiments of the invention. FIG. 38 illustrates a medical device 3800 that includes a needle 3810, a catch 3820, and a coupling member or filament 3850. The medical device also includes an anchor member 3865. The coupling member or filament 3850 is coupled to and extends from the needle 3810 to the anchor member 3865. In the illustrated embodiment, the coupling member 3850 includes a first end portion 3852 that is coupled to the needle 3810 and a second end portion 3854 that is coupled to the anchor member 3865. Any known method may be used to couple the coupling member 3850 to the needle 3810 and to the anchor 3865. For example, the coupling member 3850 may be tied, glued, molded or otherwise coupled to the needle 3810 and to the anchor 3865. In the illustrated embodiment, the coupling member 3850 is tied to the anchor 3865. In the illustrated embodiment, the anchor 3865 has a T shape.

FIG. 39 illustrates a medical device 3900 that includes a needle 3910, a catch (not illustrated), and a coupling member or filament 3950. The medical device also includes an anchor member 3965. The coupling member or filament 3950 is coupled to and extends from the needle 3910 to the anchor member 3965. In the illustrated embodiment, the coupling member 3950 includes a first end portion 3952 that is coupled to the needle 3910 and a second end portion 3954 that is coupled to the anchor member 3965. Any known method may be used to couple the coupling member 3950 to the needle 3910 and to the anchor 3965. For example, the coupling member 3950 may be tied, glued, molded or otherwise coupled to the needle 3910 and to the anchor 3965. In the illustrated embodiment, the anchor 3865 has four arms that form an X shape.

FIG. 40 illustrates a medical device 4000 that includes a needle 4010, a catch (not illustrated), and a coupling member or filament 4050. The medical device also includes an anchor member 4065. The coupling member or filament 4050 is coupled to and extends from the needle 4010 to the anchor member 4065. In the illustrated embodiment, the coupling member 4050 includes a first end portion 4052 that is coupled to the needle 4010 and a second end portion 4054 that is coupled to the anchor member 4065. Any known method may be used to couple the coupling member 4050 to the needle 4010 and to the anchor 4065. For example, the coupling member 4050 may be tied, glued, molded or otherwise coupled to the needle 4010 and to the anchor 4065. In the illustrated embodiment, coupling member 4050 is formed of a plastic or elastic material. In the illustrated embodiment, the coupling member 4050 is thicker or wider than a suture or other filament. In some embodiments, the coupling member 4050 is flexible and is tapered from one end to another end of the coupling member.

Figure 41:
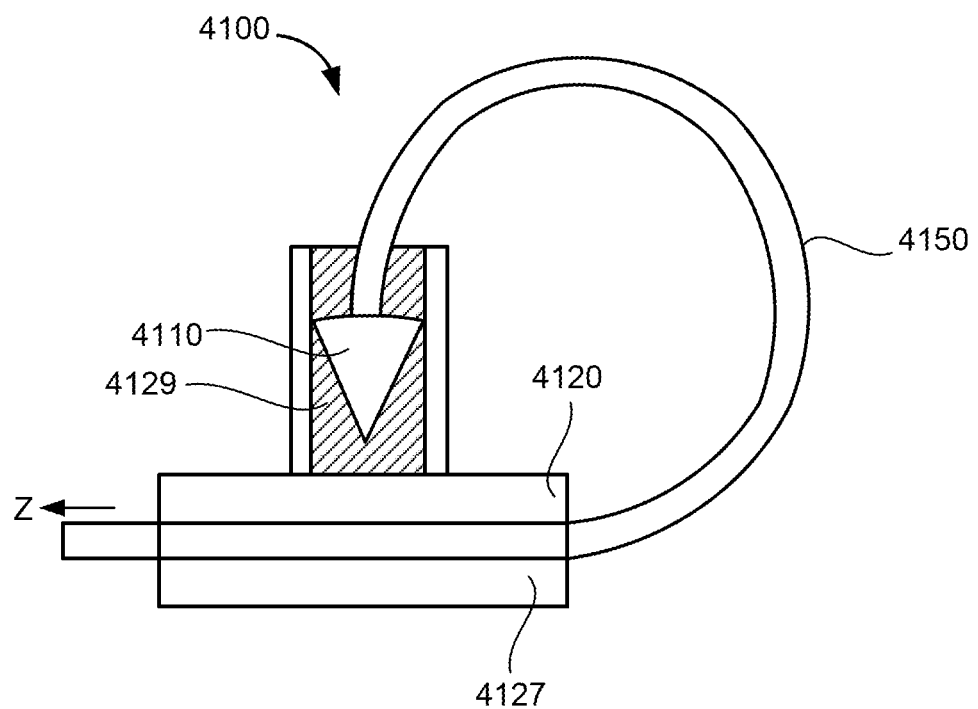

FIG. 41 is a perspective view of a medical device 4100 according to an embodiment of the invention. The medical device 4100 includes a needle 4110, a catch 4120, and a coupling member 4150. The catch 4120 is shown in see-though in FIG. 41.

In the illustrated embodiment, the medical device 4100 may be placed within a body of a patient to help couple or fix an implant within the body of the patient. For example, the needle 4110, the catch 4120, and the coupling member 4150 may collectively form a loop around or through an implant and bodily tissue to couple the implant to the bodily tissue.

In the illustrated embodiment, the coupling member 4150 is a suture and is coupled to the needle 4110. The catch 4120 is in the shape of a T and defines a first lumen 4127 and a second lumen 4129. The coupling member 4150 is configured to be passed through the first lumen 4127 and be frictionally coupled to the sidewall that forms the first lumen 4127. Accordingly, the coupling member 4150 can be passed though the first lumen 4127 and coupled therein.

The needle 4110 is configured to be coupled within the second lumen 4129. For example, in some embodiments, a sidewall of the coupling member 4150 is configured to frictionally engage the needle 4110 to couple the needle 4110 within the lumen 4129.

Accordingly, in use, the medical device 4100 can be placed within the body of a patient. The coupling member 4150 can be passed through the first lumen 4127. The coupling member 4150 can then be passed through bodily tissue and through an implant. The needle 4110 may be configured to facilitate the passing of the coupling member through the implant and the bodily tissue. The needle 4110 can then be inserted into the second lumen 4129. Once the needle 4110 is inserted into the second lumen 4129, the needle 4110 is coupled or fixed within the lumen 4129. In such an embodiment, the implant is thereby fixed or coupled to the bodily tissue via the medical device 4100.

In some embodiments, the length of size of the loop formed by the needle 4110, the catch 4120, and the coupling member 4150 may be adjustable. For example, in some embodiments, the coupling member 4150 may be pulled in the direction of arrow Z to shorten or make smaller the loop.

Figure 42:
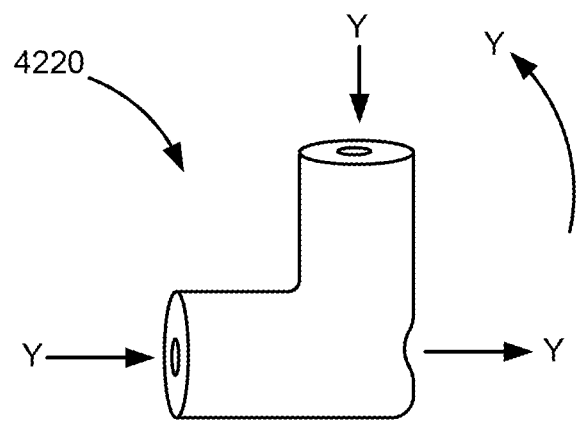

FIG. 42 illustrates a catch 4220 according to an embodiment of the invention. The catch 4220 may be of any shape or size. In the illustrated embodiment, the catch 4220 is L or elbow shaped. A coupling member may be passed along arrows Y to couple the coupling member and the needle to the catch 4220.

Figure 43:
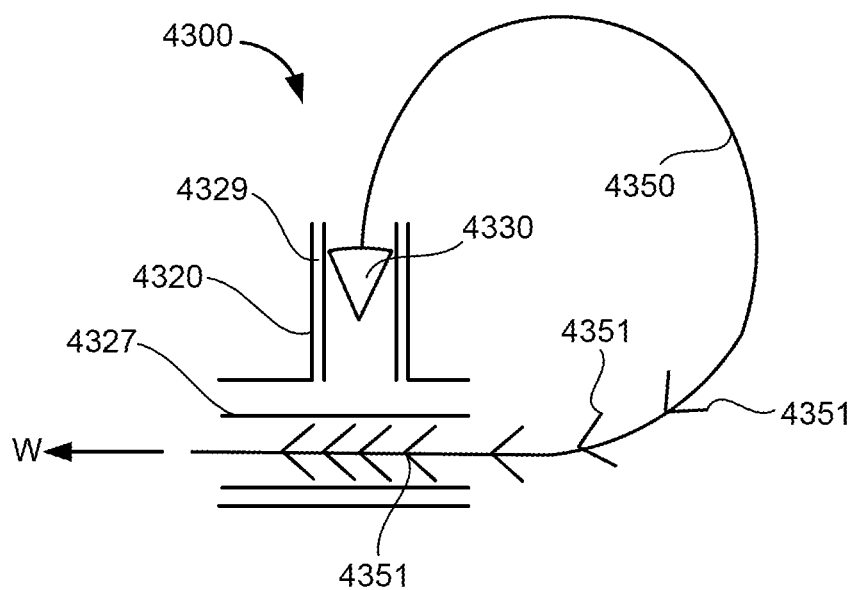

FIG. 43 is a perspective view of a medical device 4300 according to an embodiment of the invention. The medical device 4300 includes a needle 4310, a catch 4320, and a coupling member 4350. The catch 4320 is shown in see-though in FIG. 43.

In the illustrated embodiment, the medical device 4300 may be placed within a body of a patient to help couple or fix an implant within the body of the patient. For example, the needle 4310, the catch 4320, and the coupling member 4350 may collectively form a loop around or through an implant and bodily tissue to couple the implant to the bodily tissue.

In the illustrated embodiment, the coupling member 4350 is a suture and is coupled to the needle 4310. The catch 4320 is in the shape of a T and defines a first lumen 4327 and a second lumen 4329. The coupling member 4350 is configured to be passed through the first lumen 4327 and be frictionally coupled to the sidewall that forms the first lumen 4327. Accordingly, the coupling member 4350 can be passed though the first lumen 4327 and coupled therein. In the illustrated embodiment, the coupling member 4350 includes barbs or projections 4351. The barbs or projections 4351 are configured to help retain the coupling member 4350 in place within the lumen 4327. The barbs or projections 4351 may also help prevent the coupling member from being pulled out or removed from the lumen in the direction of arrow W. In some embodiments, the barbs or projections are only disposed on a portion of the coupling member so as to not allow the barbs or projections to engage or damage bodily tissue. While the illustrated embodiment shows the barbs extending in particular directions, the barbs or projections may extend in any direction or set of directions.

The needle 4310 is configured to be coupled within the second lumen 4329. For example, in some embodiments, a sidewall of the coupling member 4350 is configured to frictionally engage the needle 4310 to couple the needle 4310 within the lumen 4329.

Accordingly, in use, the medical device 4300 can be placed within the body of a patient. The coupling member 4350 can be passed through the first lumen 4327. The coupling member 4350 can then be passed through bodily tissue and through an implant. The needle 4310 may be configured to facilitate the passing of the coupling member through the implant and the bodily tissue. The needle 4310 can then be inserted into the second lumen 4329. Once the needle 4310 is inserted into the second lumen 4329, the needle 4310 is coupled or fixed within the lumen 4329. In such an embodiment, the implant is thereby fixed or coupled to the bodily tissue via the medical device 4300.

Figure 44:
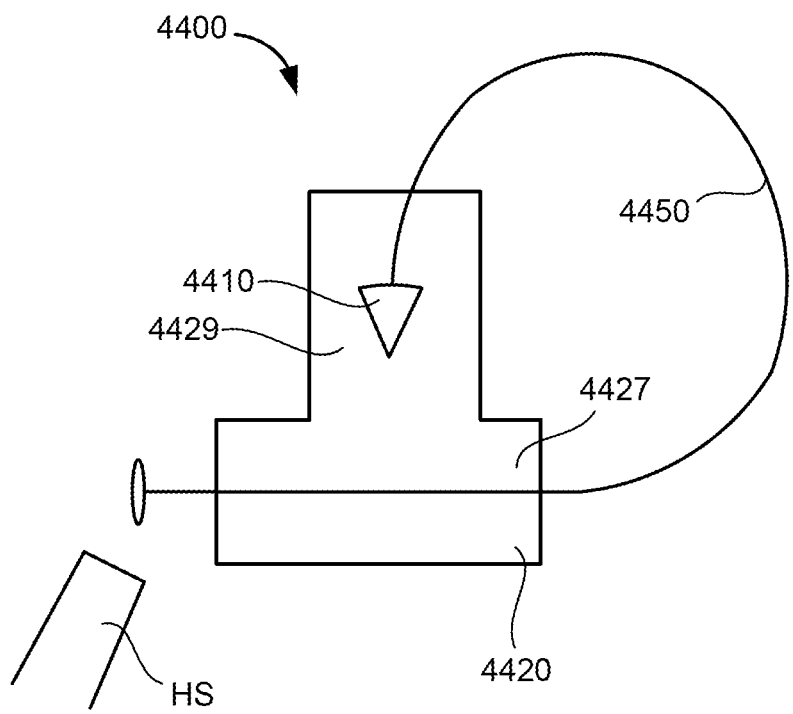

FIG. 44 is a perspective view of a medical device 4400 according to an embodiment of the invention. The medical device 4400 includes a needle 4410, a catch 4420, and a coupling member 4450. The catch 4420 is shown in see-though in FIG. 44.

In the illustrated embodiment, the medical device 4400 may be placed within a body of a patient to help couple or fix an implant within the body of the patient. For example, the needle 4410, the catch 4420, and the coupling member 4450 may collectively form a loop around or through an implant and bodily tissue to couple the implant to the bodily tissue.

In the illustrated embodiment, the coupling member 4450 is a suture and is coupled to the needle 4410. The catch 4420 is in the shape of a T and defines a first lumen 4427 and a second lumen 4429. The coupling member 4150 is configured to be passed through the first lumen 4427 and coupled to the catch 4420. For example, in the illustrated embodiment, a heat source HS may be configured to be placed proximate the coupling member to seal, melt, otherwise weld or couple the coupling member to the catch 4420.

The needle 4410 is configured to be coupled within the second lumen 4429. For example, in some embodiments, a sidewall of the coupling member 4450 is configured to frictionally engage the needle 4410 to couple the needle 4410 within the lumen 4429.

Accordingly, in use, the medical device 4400 can be placed within the body of a patient. The coupling member 4450 can be passed through the first lumen 4427. The coupling member 4450 can then be passed through bodily tissue and through an implant. The needle 4410 may be configured to facilitate the passing of the coupling member through the implant and the bodily tissue. The needle 4410 can then be inserted into the second lumen 4429. Once the needle 4410 is inserted into the second lumen 4429, the needle 4410 is coupled or fixed within the lumen 4429. The coupling member 4420 can also be coupled to the catch 4420 (such as by using the heat source). In such an embodiment, the implant is thereby fixed or coupled to the bodily tissue via the medical device 4400.

Figure 45:
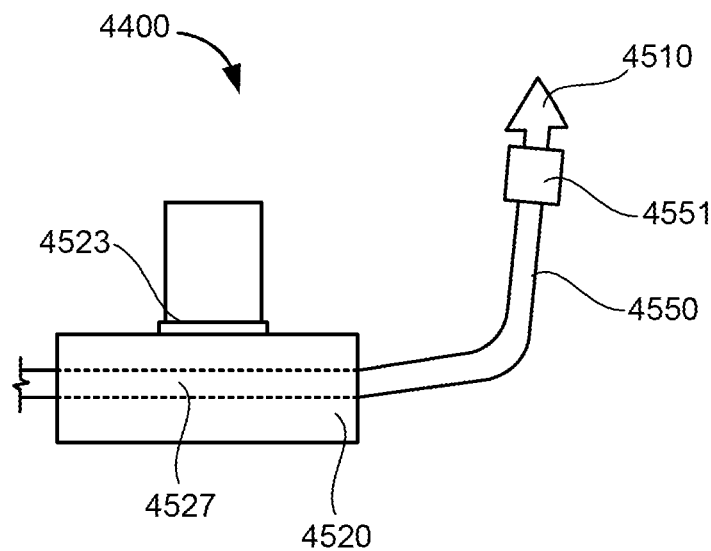
Figure 46:
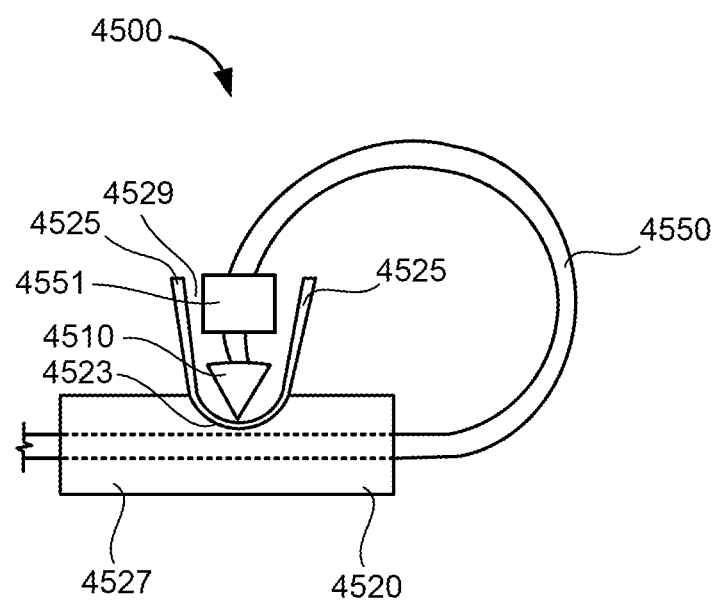

FIG. 45 are perspective views of a medical device 4500 according to an embodiment of the invention. The medical device 4500 includes a needle 4510, a catch 4520, and a coupling member 4550. The catch 4520 is shown in see-though in FIGS. 45 and 46.

In the illustrated embodiment, the medical device 4500 may be placed within a body of a patient to help couple or fix an implant within the body of the patient. For example, the needle 4510, the catch 4520, and the coupling member 4550 may collectively form a loop around or through an implant and bodily tissue to couple the implant to the bodily tissue.

In the illustrated embodiment, the coupling member 4550 is a suture and is coupled to the needle 4510. The catch 4520 is in the shape of a T and defines a first lumen 4527 and a second lumen 4529. The coupling member 4550 is configured to be passed through the first lumen 4527 and be frictionally coupled to the sidewall that forms the first lumen 4527. Accordingly, the coupling member 4550 can be passed though the first lumen 4527 and coupled therein.

The needle 4510 is configured to be coupled within the second lumen 4529. For example, in the illustrated embodiment, the catch 4520 includes a flexible or bendable element or member 4523. The needle 4510 is configured to be inserted into the lumen 4529 and contact the flexible or bendable member 4523. The needle 4510 or the force of the needle 4510 contacting the flexible or bendable member 4523 may cause the member 4523 to bend. In the illustrated embodiment, the bending of the member 4523 is configured to close or partially close the first lumen 4527 to help engage and retain the coupling member 4550 within the first lumen 4527. In the illustrated embodiment, the flexible member 4523 includes wings or projections 4525 that are configured to wrap around or grasp a portion 4551 of the coupling member 4550 to help retain the needle 4510 within the second lumen 4529.

Accordingly, in use, the medical device 4500 can be placed within the body of a patient. The coupling member 4550 can be passed through the first lumen 4527. The coupling member 4550 can then be passed through bodily tissue and through an implant. The needle 4510 may be configured to facilitate the passing of the coupling member through the implant and the bodily tissue. The needle 4510 can then be inserted into the second lumen 4529. Once the needle 4510 is inserted into the second lumen 4529, the needle 4510 is coupled or fixed within the lumen 4529. In such an embodiment, the implant is thereby fixed or coupled to the bodily tissue via the medical device 4500.

Figure 47:
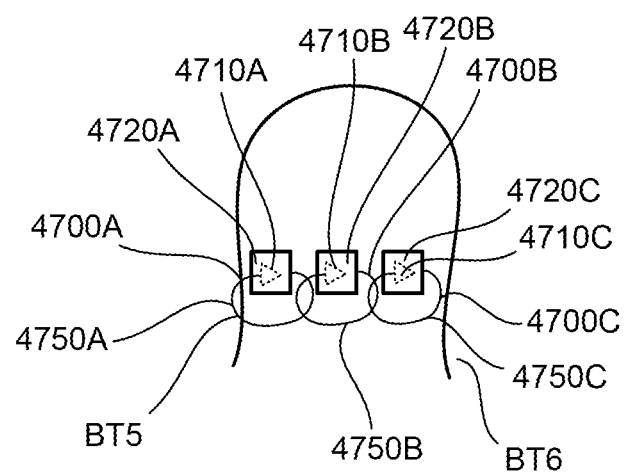
FIG. 47 is a schematic view of a device disposed within a body of a patient according to an embodiment of the invention.

FIG. 47 is a schematic view of medical devices disposed within a body of a patient. In the illustrated embodiment, several devices are disposed in the form a loops to connect two pieces of bodily tissue BT5 and BT6. Specifically, a first device 4700A includes a needle 4710A, a catch 4720A, and a coupling member 4750A is coupled to the first bodily tissue BT5 and is in the form of a loop. A second device 4700B includes a needle 4710B, a catch 4720B, and a coupling member 4750B is coupled to the first device 4700A and is in the form of a loop. A third device 4700C includes a needle 4710C, a catch 4720C, and a coupling member 4750C is coupled to the second device 4700B and the second bodily tissue BT6 and is in the form of a loop.

Although three devices are shown in the illustrated embodiment, any number of devices may be used.

Figure 48:
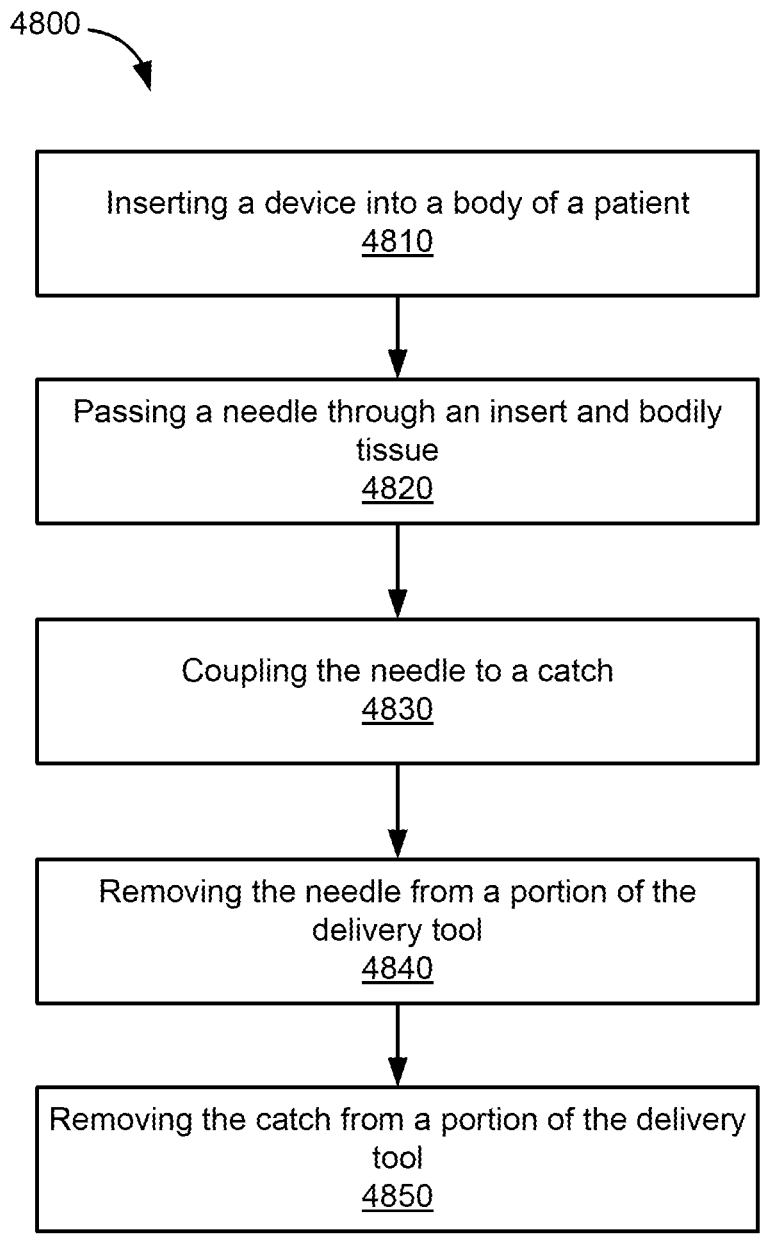
FIG. 48 is a flow chart of a method according to an embodiment of the invention.

FIG. 48 is a flow chart that illustrates a method 4800 according to an embodiment of the invention. At 4810, a medical device is inserted into the body of the patient. In some embodiments, the device is inserted into a pelvic region of a patient through, for example, a vaginal incision. In other embodiments, the device may be inserted into other locations of the body.

At 4820, a needle of the device is passed through bodily tissue. In some embodiments, the passing of the needle includes moving the needle through bodily tissue via a carrier that is actuated by a plunger or actuation device or member.

At 4830, the needle is caught by a catch of the device. For example, in some embodiments, the needle is moved into a lumen or opening defined by the catch and is coupled to the catch.

At 4840, the needle is removed from a portion of the delivery device. For example, in some embodiments, the needle is removed or decoupled from the carrier of the delivery device.

At 4850, the catch is removed from a portion of the delivery device. In some embodiments, the delivery device may then be removed from the body of the patient leaving the needle, a coupling member and the catch within the body of the patient. In some embodiment, the needle, coupling member and the catch are configured to help retain an implant in place within a body of the patient.

In some embodiments, a medical device includes a needle and a catch. The catch has a body portion. The body portion of the catch defines a cavity. The catch is configured to be coupled to the needle such that at least a portion of the needle is disposed within the cavity.

In some embodiments, the needle is configured to pierce bodily tissue. In some embodiments, the needle includes a tissue piercing portion, the tissue piercing portion being configured to be disposed within the cavity when the needle is coupled to the catch.

In some embodiments, the device includes a coupling member having a first end portion coupled to the needle and a second end portion coupled to the catch.

In some embodiments, the body of the catch includes an upper portion, a lower portion and two side portions, the upper portion, the lower portion and the two side portions collectively define the cavity.

In some embodiments, the needle is a first needle, the catch is a first catch, the medical device further includes a second needle and a second catch. The second catch is configured to be coupled to the second needle.

In some embodiments, the needle is a first needle, the catch is a first catch, the medical device further includes a second needle and a second catch. The second catch is configured to be coupled to the second needle. A filament has a first end portion coupled to the first needle and a second end portion coupled to the second needle.

In some embodiments, the catch includes an attachment portion, the attachment portion is configured to engage a delivery tool to removably couple the catch to the delivery tool.

In some embodiments, the catch includes an attachment portion, the attachment portion is configured to engage a delivery tool to frictionally couple the catch to the delivery tool.

In some embodiments, the catch includes an attachment portion, the attachment portion is configured to engage a delivery tool to removably couple the catch to the delivery tool, the needle being configured to be removably coupled to a carrier portion of the delivery tool.

In some embodiments, a medical device includes a delivery tool, a needle, and a catch. The delivery tool has a receiving portion and a carrier portion. The needle is configured to be removably coupled to a carrier portion of the delivery tool. The catch has a body portion, the body portion of the catch defining a cavity, the catch being configured to be coupled to the needle such that at least a portion of the needle is disposed within the cavity, the catch being configured to be removably coupled to the receiving portion of the delivery tool.

In some embodiments, the catch includes an attachment portion that is configured to frictionally couple the catch to the receiving portion of the delivery tool.

In some embodiments, the needle is configured to be pierce bodily tissue.

In some embodiments, the needle includes a tissue piercing portion, the tissue piercing portion being configured to be disposed within the cavity when the needle is coupled to the catch.

In some embodiments, the device includes a filament having a first end portion coupled to the needle and a second end portion coupled to the catch.

In some embodiments, a method of coupling an implant to bodily tissue of a patient includes inserting a device into a body of the patient, the device having a delivery tool, a catch removably coupled to a first portion of the delivery tool, and a needle removably coupled to a second portion of the delivery tool; passing the needle through the implant and bodily tissue; coupling the needle to the catch; removing the needle from the second portion of the delivery tool; and removing the catch from the first portion of the delivery tool.

In some embodiments, the method includes removing the delivery tool from the body of the patient.

In some embodiments, the method includes moving a portion of the needle into a cavity defined by the catch.

In some embodiments, the device includes a filament having a first end portion coupled to the catch and a second end portion coupled to the needle.

In some embodiments, the removing the catch from the first portion of the delivery tool includes moving a lock member with respect to the delivery tool to release the catch from the delivery tool While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device for treatment of a pelvic condition, comprising:
 a needle having a needle head; and
 a catch having a body portion and a base portion, the body portion of the catch having a sidewall with an inner surface defining a funnel shaped cavity and a first opening in communication with the funnel shaped cavity, the first opening being larger than the needle head, the catch being configured to be coupled to the needle such that at least a portion of the needle is moved into the cavity via the first opening, the catch including a projection member extending from the sidewall inner surface and being configured to engage the needle to help couple the needle to the catch, the catch including a retention member configured to engage bodily tissue when the catch is disposed within a body of a patient.

2. The medical device of claim 1, wherein the needle is configured to pierce the bodily tissue.

3. The medical device of claim 1, wherein the needle head of the needle includes a tissue piercing portion, the tissue piercing portion being configured to be disposed within the cavity when the needle is coupled to the catch.

4. The medical device of claim 1, further comprising:
a coupling member having a first end portion coupled to the needle and a second end portion coupled to the catch.

5. The medical device of claim 1, wherein the catch includes an attachment portion, the attachment portion is configured to engage a delivery tool to removably couple the catch to the delivery tool.

6. The medical device of claim 1, wherein the catch includes an attachment portion, the attachment portion is configured to engage a delivery tool to frictionally couple the catch to the delivery tool.

7. The medical device of claim 1, wherein the catch includes an attachment portion, the attachment portion is configured to engage a delivery tool to removably couple the catch to the delivery tool, the needle being configured to be removably coupled to a carrier portion of the delivery tool.

8. The medical device of claim 1, wherein the retention member extends from an outer surface of the sidewall.

9. The medical device of claim 1, wherein the retention member is a first retention member, the catch includes a second retention member.

10. A medical device for treatment of a pelvic condition, comprising:
a delivery tool having a distal end portion, the distal end portion defining an opening, the distal end portion including a receiving portion and a carrier portion, the carrier portion configured to move out of the opening and towards the receiving portion, the receiving portion being disposed proximally from the opening;
a needle, the needle being configured to be removably coupled to the carrier portion of the delivery tool; and
a catch having a body portion and a base portion, the base portion being configured to prevent the needle from extending from the base portion, the body portion of the catch having a first opening portion and a sidewall having an inner surface defining a cavity, the catch being configured to be removably coupled to the receiving portion of the delivery tool such that the catch is configured to remain stationary with respect to the delivery tool as the carrier moves the needle towards the catch, the catch including a retention member configured to engage bodily tissue when the catch is disposed within a body of a patient.

11. The medical device of claim 10, wherein the catch includes an attachment portion that is configured to frictionally couple the catch to the receiving portion of the delivery tool.

12. The medical device of claim 10, wherein the needle is configured to pierce the bodily tissue.

13. The medical device of claim 10, wherein the needle includes a tissue piercing portion, the tissue piercing portion being configured to be disposed within the cavity when the needle is coupled to the catch.

14. The medical device of claim 10, further comprising:
a filament having a first end portion coupled to the needle and a second end portion coupled to the catch.

15. The medical device of claim 10, wherein the cavity defined by the sidewall inner surface is funnel shaped.

16. The medical device of claim 10, wherein the cavity defined by the sidewall inner surface is funnel shaped, the catch includes a projection extending from the sidewall inner surface.

17. The medical device of claim 10, wherein the retention member extends from an outer surface of the sidewall.

18. The medical device of claim 10, wherein the retention member is a first retention member, the catch includes a second retention member.

* * * * *